(12) United States Patent
Sun et al.

(10) Patent No.: US 11,814,371 B2
(45) Date of Patent: Nov. 14, 2023

(54) HETEROCYCLIC COMPOUND

(71) Applicant: MEDSHINE DISCOVERY INC., Nanjing (CN)

(72) Inventors: Guanglong Sun, Shanghai (CN); Chunli Shen, Shanghai (CN); Chengde Wu, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 65 days.

(21) Appl. No.: 17/905,538

(22) PCT Filed: Mar. 4, 2021

(86) PCT No.: PCT/CN2021/079093
§ 371 (c)(1),
(2) Date: Sep. 2, 2022

(87) PCT Pub. No.: WO2021/175290
PCT Pub. Date: Sep. 10, 2021

(65) Prior Publication Data
US 2023/0167098 A1 Jun. 1, 2023

(30) Foreign Application Priority Data
Mar. 4, 2020 (CN) .......................... 202010144412.8

(51) Int. Cl.
*C07D 405/14* (2006.01)
*C07D 401/14* (2006.01)

(52) U.S. Cl.
CPC ............... *C07D 405/14* (2013.01); *C07D 401/14* (2013.01)

(58) Field of Classification Search
CPC ..................... C07D 405/14; C07D 401/14
USPC ........................................................ 546/256
See application file for complete search history.

(56) References Cited

FOREIGN PATENT DOCUMENTS

| | | |
|---|---|---|
| CN | 101495468 A | 7/2009 |
| CN | 103080104 A | 5/2013 |
| CN | 105452240 A | 3/2016 |
| CN | 106257976 A | 12/2016 |
| CN | 109311847 A | 2/2019 |
| CN | 110577519 A | 12/2019 |
| CN | 111432803 A | 7/2020 |
| WO | 2008016883 A2 | 2/2008 |
| WO | 2012017020 A1 | 2/2012 |
| WO | 2014188211 A1 | 11/2014 |
| WO | 2015134998 A1 | 9/2015 |
| WO | 2016083820 A1 | 6/2016 |
| WO | 2017207983 A1 | 12/2017 |
| WO | 2019106361 A1 | 6/2019 |

OTHER PUBLICATIONS

Written Opinion of the International Searching Authority issued in International Patent Application No. PCT/CN2021/079093 mailed on Jun. 3, 2021, 6 pages including English Translation.
Intenational Search Report issued in International Patent Application No. PCT/CN2021/079093 mailed on Jun. 3, 2021, 12 pages including English Translation.

*Primary Examiner* — Kahsay Habte
(74) *Attorney, Agent, or Firm* — MH2 Technology Law Group LLP

(57) ABSTRACT

The present application relates to the field of medicine. Specifically, disclosed are a compound of formula (I), a preparation method therefor, and a pharmaceutical composition comprising the compound.

10 Claims, No Drawings

HETEROCYCLIC COMPOUND

The present application is a U.S. National Stage application of PCT/CN2021/079093 filed Mar. 4, 2021, which claims priority to Chinese application No. 202010144412.8 filed Mar. 04, 2020, the entire disclosures of which are hereby incorporated by reference in their entireties.

TECHNICAL FIELD

The present disclosure belongs to the field of medicine, specifically relates to a compound of formula (I), a preparation method therefor and a pharmaceutical composition comprising the compound.

BACKGROUND

Plasma kallikrein (PKal), also known as Fletcher factor, is specifically expressed in hepatocytes and is a glycoprotein with high molecular weight; it is produced by FXIIa acting on prokallikrein and can mediate the cleavage of prokallikrein to produce bradykinin (BK), activate its B1 receptor and B2 receptor, regulate vascular tension, inflammatory response, and endogenous blood coagulation and fibrinolysis processes. PKal is often highly expressed in diabetic patients, which leads to the increase of vasodilation and vascular permeability (RVP), thereby causing diabetic retinopathy (DR) and diabetic macular edema (DME). The main function of plasma kallikrein inhibitor is to reduce the level of plasma kallikrein in vivo and reduce the activation of bradykinin on two receptors, thus alleviating vascular permeability and inflammation to achieve an important role in treating diabetic retinopathy and diabetic macular edema. The plasma kallikrein inhibitor KVD001 (WO2013005045), developed by KalVista Pharmaceuticals, is in clinical phase II and is administered via intravitreal injection for the treatment of diabetic macular edema, and patient compliance needs to be improved.

In view of the important role of plasma kallikrein inhibitors and the compliance of patients with current administration methods, it is particularly important to develop plasma kallikrein inhibitors suitable for oral therapeutic drugs.

CONTENT OF THE PRESENT INVENTION

The present disclosure provides a compound of formula (I) or a pharmaceutically acceptable salt thereof, (I)

wherein,
$R_1$ is H, F, Cl, Br, I, OH or $NH_2$;
$R_2$ is H, F, Cl, Br, I, OH or $NH_2$;
$R_3$ is H, F, Cl, Br, I, OH, $C_{1-3}$ alkyl or $C_{1-3}$ alkoxy, wherein the $C_{1-3}$ alkyl and $C_{1-3}$ alkoxy are each independently and optionally substituted by 1, 2 or 3 $R_a$;
$R_4$ is H or $C_{1-3}$ alkyl, wherein the $C_{1-3}$ alkyl is optionally substituted by 1, 2 or 3 $R_b$;
$T_1$ is N or $CR_5$;
$T_2$ is N or $CR_6$;
$T_3$ is N or $CR_7$;
$E_1$ is O or $NR_8$;
$R_5$, $R_6$ and $R_7$ are each independently H, F, Cl, Br, I, OH or $NH_2$;
$R_8$ is H, $C_{1-3}$ alkyl, $C_{1-3}$ alkoxy, —C(=O)$C_{1-3}$ alkyl or —S(=O)$_2C_{1-3}$ alkyl, wherein the $C_{1-3}$ alkyl, —$C_{1-3}$ alkoxy, —C(=O)$C_{1-3}$ alkyl and —S(=O)$_2C_{1-3}$ alkyl are each independently and optionally substituted by 1, 2 or 3 $R_c$;
$R_a$, $R_b$ and $R_c$ are each independently F, Cl, Br, I, OH or $NH_2$.

In some embodiments of the present disclosure, $R_3$ is H, F, Cl, Br, I, OH, $CH_3$ or —O—$CH_3$, wherein the $CH_3$ or —O—$CH_3$ are each independently and optionally substituted by 1, 2 or 3 $R_a$, and $R_a$ and the other variables are as defined in the present disclosure.

In some embodiments of the present disclosure, $R_3$ is —O—$CH_3$, and the other variables are as defined in the present disclosure.

In some embodiments of the present disclosure, $R_4$ is H or $CH_3$, wherein the $CH_3$ is optionally substituted by 1, 2, or 3 $R_b$, and $R_b$ and the other variables are as defined in the present disclosure.

In some embodiments of the present disclosure, $R_4$ is H or $CH_3$, and the other variables are as defined in the present disclosure.

In some embodiments of the present disclosure, $R_8$ is H, $CH_3$, $CH_2$—$CH_3$, —C(=O)—$CH_3$ or —S(=O)$_2$—$CH_3$, wherein the $CH_3$, $CH_2$—$CH_3$, —C(=O)—$CH_3$ or —S(=O)$_2$—$CH_3$ is optionally substituted by 1, 2 or 3 $R_c$, and $R_c$ and the other variables are as defined in the present disclosure.

In some embodiments of the present disclosure, $R_8$ is H, $CH_3$, $CH_2$—$CF_3$, —C(=O)—$CH_3$ or —S(=O)$_2$—$CH_3$, and the other variables are as defined in the present disclosure.

Other embodiments of the present disclosure are derived from any combination of above variables.

In some embodiments of the present disclosure, the compound has the structure of (I-1) or (I-2)

(I-1)

(I-2)

wherein, $T_1$, $T_2$, $T_3$, $R_1$, $R_2$, $R_3$, $R_4$ and $R_8$ are as defined in the present disclosure.
The present disclosure also provides a compound of the following formula or a pharmaceutically acceptable salt thereof:
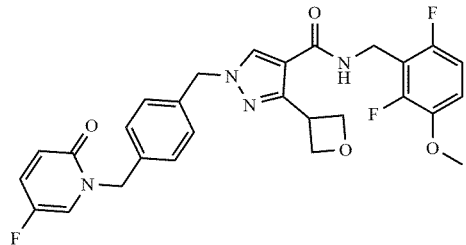 [SMILES: COc1ccc(F)c(CNC(=O)c2cn(Cc3ccc(Cn4cc(F)ccc4=O)cc3)nc2C2COC2)c1F]
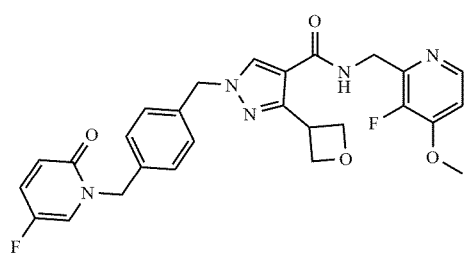 [SMILES: COc1ccnc(CNC(=O)c2cn(Cc3ccc(Cn4cc(F)ccc4=O)cc3)nc2C2COC2)c1F]
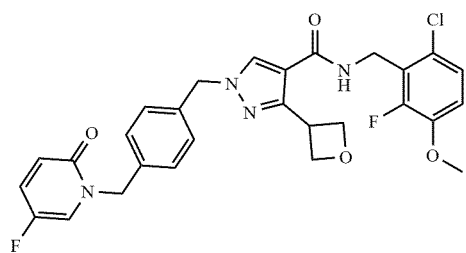 [SMILES: COc1ccc(Cl)c(CNC(=O)c2cn(Cc3ccc(Cn4cc(F)ccc4=O)cc3)nc2C2COC2)c1F]
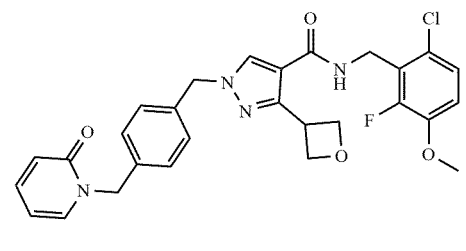 [SMILES: COc1ccc(Cl)c(CNC(=O)c2cn(Cc3ccc(Cn4ccccc4=O)cc3)nc2C2COC2)c1F]
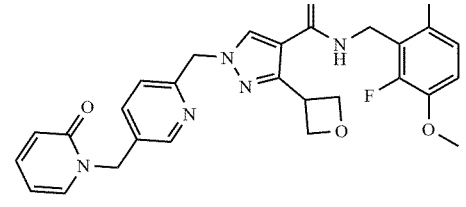
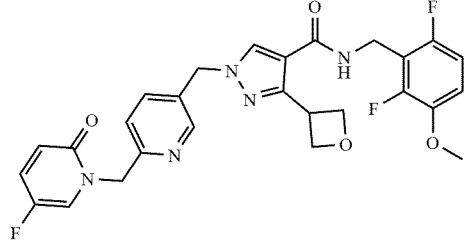 [SMILES: COc1ccc(F)c(CNC(=O)c2cn(Cc3ccc(Cn4cc(F)ccc4=O)nc3)nc2C2COC2)c1F]
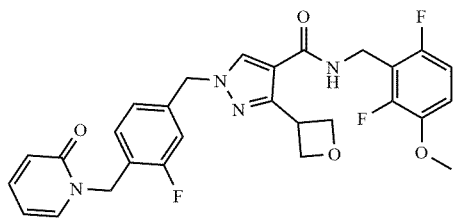 [SMILES: COc1ccc(F)c(CNC(=O)c2cn(Cc3ccc(Cn4ccccc4=O)c(F)c3)nc2C2COC2)c1F]
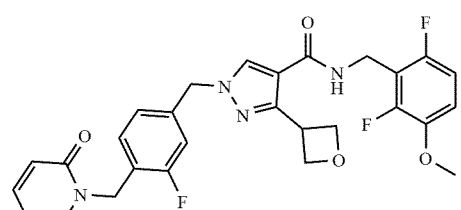
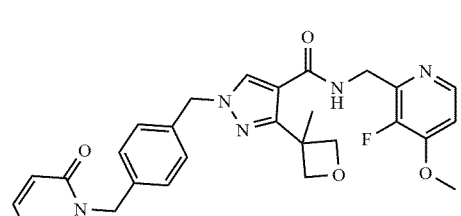
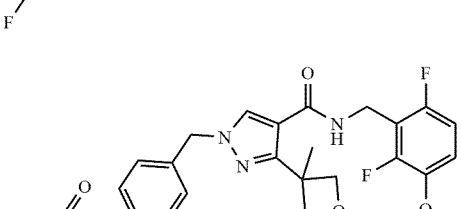
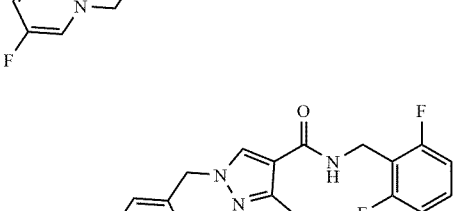
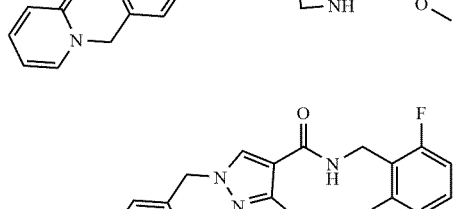
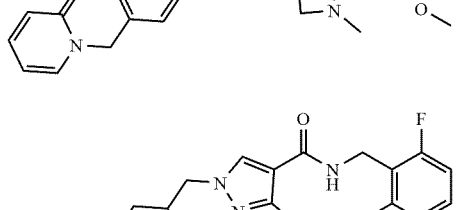

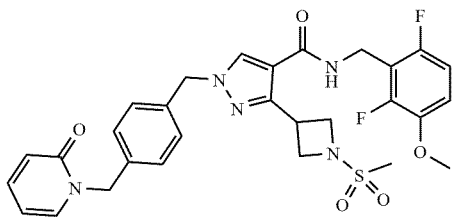 [SMILES: COc1ccc(F)c(CNC(=O)c2cn(Cc3ccc(Cn4ccccc4=O)cc3)nc2C2CN(S(C)(=O)=O)C2)c1F]

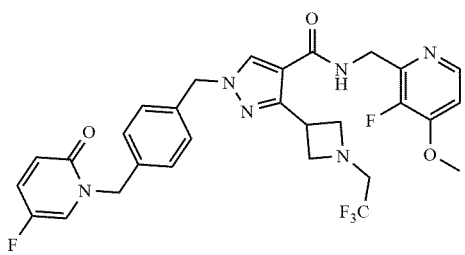 [SMILES: COc1ccnc(CNC(=O)c2cn(Cc3ccc(Cn4cc(F)ccc4=O)cc3)nc2C2CN(CC(F)(F)F)C2)c1F]

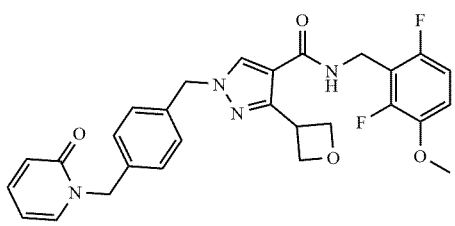 [SMILES: COc1ccc(F)c(CNC(=O)c2cn(Cc3ccc(Cn4ccccc4=O)cc3)nc2C2COC2)c1F]

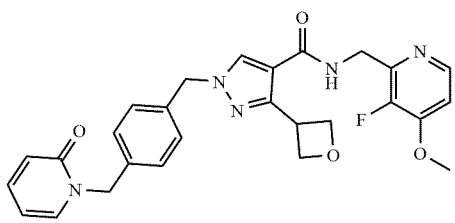 [SMILES: COc1ccnc(CNC(=O)c2cn(Cc3ccc(Cn4ccccc4=O)cc3)nc2C2COC2)c1F]

or

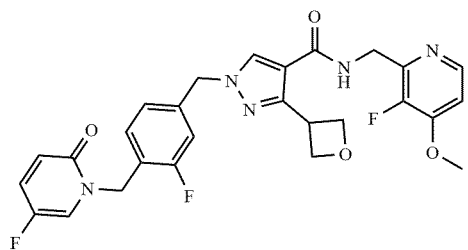

In some embodiments of the present disclosure, the compound or the pharmaceutically acceptable salt thereof, wherein the salt is hydrochloride.

The present disclosure also provides a use of the compound or the pharmaceutically acceptable salt thereof in the manufacture of a medicament related to plasma kallikrein inhibitors.

In some embodiments of the present disclosure, a use of the hydrochloride in the manufacture of a medicament related to plasma kallikrein inhibitors.

Technical Effect

The compounds of the present disclosure exhibit significant plasma kallikrein inhibitory activity. The compounds of the present disclosure exhibit good oral PK property and appropriate eye exposure, and display obvious relief effect on retinal edema by oral administration in an animal model of diabetic macular edema induced by carbonic anhydrase (CA-1).

Definition and Description

Unless otherwise indicated, the following terms and phrases used herein are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure.

"optional" or "optionally" means that the subsequent event or condition may occur but not requisite, that the term includes the instance in which the event or condition occurs and the instance in which the event or condition does not occur.

The term "substituted" means one or more than one hydrogen atom (s) on a specific atom are substituted with the substituent, the substituent including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include, but are not limited to methyl (Me), ethyl (Et), propyl (including n-propyl and isopropyl) and the like.

Unless otherwise specified, the term "$C_{1-3}$ alkoxy" refers to an alkyl containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and also includes any ranges from n to n+m, e.g., $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n-membered to n+m-membered means that the number of atoms on the ring is n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and also includes any ranges from n to n+m, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring and the like.

The term "leaving group" refers to a functional group or atom which can be replaced by another functional group or atom through a substitution reaction (such as nucleophilic substitution reaction). For example, representative leaving groups include triflate; chlorine, bromine, iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "sulfhydryl protecting group". The term "amino protecting group" refers to a protecting group suitable for blocking the side reaction on the nitrogen of an amino. Representative amino protecting groups include, but are not limited to: formyl; acyl, such as chain alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4′-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as chain alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyldimethylsilyl (TBS) and the like.

The compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art, and preferred embodiments include, but are not limited to, the embodiments of the present disclosure.

The structure of the compound of the present disclosure can be confirmed by conventional methods well known to those skilled in the art and if the present disclosure relates to the absolute configuration of the compound, the absolute configuration can be confirmed by conventional technical means in the art. For example, using single crystal X-ray diffraction (SXRD), the diffraction intensity data of the cultured single crystals were collected by Bruker D8 venture diffractometer with CuKα as light source and scanning mode of φ/ω scan, and after collecting the relevant data, the absolute configuration can be confirmed by further analyzing the crystal structure by direct method (Shelxs97).

The solvents used in the present disclosure are commercially available. The present disclosure employs the following abbreviations: aq stands for water.

Compounds are named according to conventional naming principles in the art or by ChemDraw® software, and the commercially available compounds use their vendor directory names.

DETAILED DESCRIPTION OF THE EMBODIMENTS

The present disclosure is described in detail by the embodiments below, but the present disclosure is not limited thereto. The present disclosure has been described in detail herein, and its specific embodiments have also been disclosed; for one skilled in the art, it is obvious to make various modifications and improvements to the embodiments of the present disclosure without departing from the spirit and scope of the present disclosure. All solvents used in the present disclosure are commercially available and can be directly used without further purification. The raw materials of the initial compound used for synthesis in the present disclosure are commercially available, and can also be prepared by methods in the prior art.

Embodiment 1

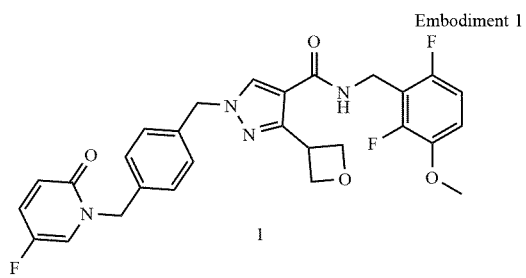

Synthetic route:

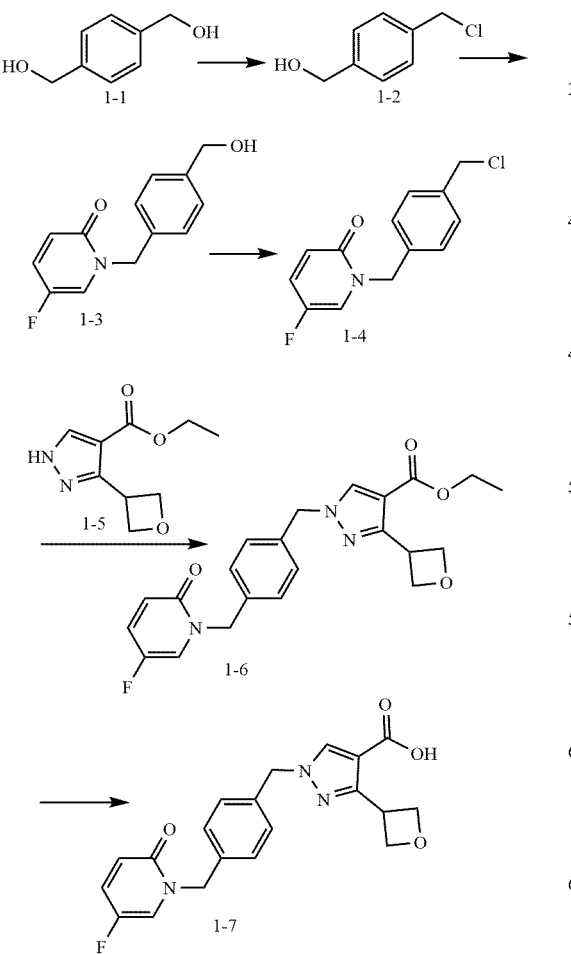

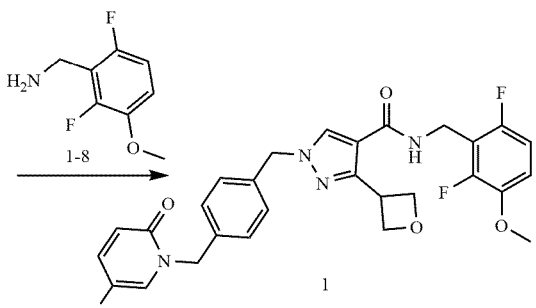

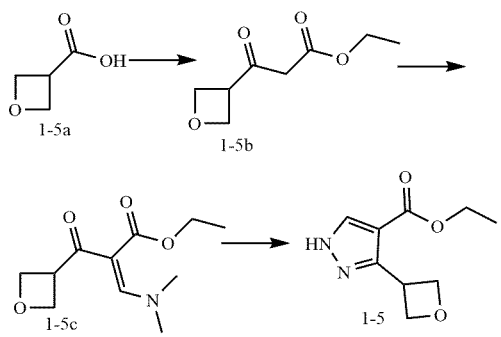

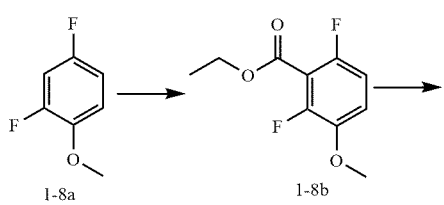

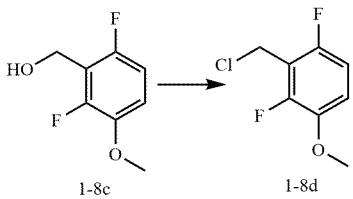

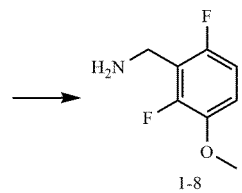

1) Synthesis of Compound 1-2

Compound 1-1 (92 g, 665.88 mmol), hydrochloric acid (12 M, 277.45 mL) and anhydrous toluene (920 mL) were added to a three-necked flask, and the mixture was stirred for 4 hours at 25° C. Saturated sodium bicarbonate aqueous solution was added thereto to adjust the pH to 7, and then ethyl acetate (300 mL*3) was added for extraction, and the organic phases were collected, combined, and washed by adding saturated brine (500 mL), and the organic phase was seperated, dried by adding anhydrous sodium sulfate, filtered, and the filtrate was concentrated under reduced pressure to obtain compound 1-2. LCMS (ESI) m/z: 139 [M-17]$^+$.

2) Synthesis of Compound 1-3

5-Fluoro-2-hydroxypyridine (14.7 g, 130.26 mmol), compound 1-2 (17.0 g, 108.55 mmol), N,N-dimethylformamide (160 mL) and potassium carbonate (15.0 g, 108.55 mmol) were added to a pre-dried single-necked flask, and the mixture was stirred at 65° C. for 18 hours. After the system was naturally cooled down to 40° C., the system was filtered, and the filter cake was rinsed with ethyl acetate (100 mL*3), and the filtrate was collected. Saturated brine (200 mL) was added thereto, and the mixture was extracted with ethyl acetate (300 mL*3), then the organic phases were collected, dried by adding anhydrous sodium sulfate, filtered, and the filtrate was concentrated to dryness under reduced pressure to obtain the crude product of an oil. Ethyl acetate (40 mL) was added to the crude product, and the mixture was stirred at 25° C. for 10 minutes, filtered, and the filter cake was rinsed with ethyl acetate (10 mL*3), and the filter cake was collected and dried under vacuum to obtain compound 1-3. LCMS (ESI) m/z: 234 [M+1]$^+$.

3) Synthesis of Compound 1-4

Dichloromethane (25 mL), compound 1-3 (2.2 g, 8.49 mmol), triethylamine (1.3 g, 12.73 mmol) were added to a pre-dried reaction flask, and the temperature was cooled down to 0° C., then methylsulfonyl chloride (1.4 g, 11.88 mmol) was added dropwise. After the dropwise addition was completed, the mixture was warmed up to 20° C. and stirred for 16 hours. The reaction mixture was diluted with dichloromethane (20 mL), added with water (50 mL) and stirred for 10 minutes, then the aqueous phase was removed, and the organic phase was dried over anhydrous sodium sulfate, filtered, and concentrated under reduced pressure to obtain compound 1-4. $^1$HNMR (400 MHz, CDCl$_3$) δ ppm 7.36-7.43 (m, 2 H), 7.31 (d, J=8.2 Hz, 2 H), 7.24-7.29 (m, 1 H), 7.16 (t, J=3.6 Hz, 1 H), 6.61 (dd, J=5.4, 10.0 Hz, 1 H), 5.10 (s, 2 H), 4.58 (s, 2 H); LCMS (ESI) m/z: 252 [M+1]$^+$.

4) Synthesis of Compound 1-5b

Compound 1-5a (0.5 g, 4.90 mmol), carbonyl diimidazole (953 mg, 5.88 mmol), tetrahydrofuran (5 mL) were added to a round-bottom flask, and the mixture was stirred at room temperature of 25° C. for 2 hours, and then ethyl potassium malonate (1.0 g, 5.88 mmol) and magnesium chloride (574 mg, 6.02 mmol) were added thereto, and the mixture was stirred at 25° C. for 16 hours, and the reaction mixture was added with ethyl acetate (20 mL) and water (10 mL), then the aqueous phase was removed, and the organic phase was dried over anhydrous sodium sulfate, filtered, and concentrated under reduced pressure to obtain the crude product. The crude product was purified by column chromatography (gradient elution: 0 to 100 % ethyl acetate/petroleum ether, flow rate of 20 mL/min) to obtain compound 1-5b. $^1$HNMR (400 MHz, CDCl$_3$) δ ppm 4.75-4.87 (m, 4 H), 4.20 (m, 2 H), 4.07-4.16 (m, 1 H), 3.47 (s, 2 H), 1.22-1.33 (m, 3 H).

5) Synthesis of Compound 1-5c

Compound 1-5b (3.5 g, 20.33 mmol) dissolved in N,N-dimethylformamide (35 mL) was added to a pre-dried reaction flask, then N,N-dimethylformamide dimethyl acetal (4.8 g, 40.66 mmol) was added thereto. The mixture was stirred at 120° C. for 2 hours, and the system was cooled down to 20° C., concentrated under reduced pressure to obtain compound 1-5c. $^1$HNMR (400 MHz, CDCl$_3$) δ ppm 7.80 (s, 1 H), 4.80 (s, 2 H), 4.78 (s, 2 H), 4.23-4.35 (m, 1 H), 4.15 (m, 2 H), 3.21-3.36 (m, 3 H), 2.80-2.90 (m, 3 H), 1.29 (m, 3 H).

6) Synthesis of Compound 1-5 n-Butanol (10 mL), 1-5c (4.6 g, 20.24 mmol), hydrazine monohydrate (1.3 g, 24.29 mmol), acetic acid (1.5 g, 24.29 mmol) were added to a pre-dried reaction flask, and the mixture was stirred at 120° C. for 2 hours, then the system was cooled down to 20° C. Ethyl acetate (50 mL) and saturated sodium bicarbonate aqueous solution (50 mL) were added to the reaction mixture and stirred for 10 min, then the aqueous phase was removed, and the organic phase was dried over anhydrous sodium sulfate, filtered and concentrated under reduced pressure to obtain compound 1-5. $^1$HNMR (400 MHz, CD$_3$OD) δ ppm 7.85-8.23 (m, 1 H), 5.00-5.06 (m, 2 H), 4.93 (m, 2 H), 4.57-4.84 (m, 1 H), 4.25 (m, 2 H), 1.33 (t, J=7.2 Hz, 3 H).

7) Synthesis of Compound 1-6

N,N-Dimethylformamide (5 mL), compound 1-4 (389 mg, 1.99 mmol), 1-5 (0.5 g, 1.99 mmol), and potassium carbonate (549 mg, 3.97 mmol) were added to a pre-dried reaction flask, and the reaction was carried out at 80° C. for 16 hours, then the system was cooled down to 20° C., and water (10 mL) was added to the system. The mixture was filtered, and the filter cake was washed with water (20 mL), collected and dried under vacuum to obtain compound 1-6. $^1$HNMR (400 MHz, CDCl$_3$) δ ppm 7.83 (s, 1 H), 7.32-7.37 (m, 2 H), 7.26-7.31 (m, 3 H), 7.18 (t, J=3.6 Hz, 1 H), 6.62 (dd, J=5.4, 10.0 Hz, 1 H), 5.29 (s, 2 H), 5.11 (s, 2 H), 4.94-5.08 (m, 4 H), 4.65 (m, 1 H), 4.24 (m, 2 H), 1.33 (t, J=7.2 Hz, 3 H).

8) Synthesis of Compound 1-7

Tetrahydrofuran (12 mL), methanol (3 mL), compound 1-6 (0.65 g, 1.58 mmol), water (3 mL), and lithium hydroxide monohydrate (199 mg, 4.74 mmol) were added to a pre-dried reaction flask. The mixture was stirred at 70° C. for 2 hours, and the system was cooled down to 20° C., then the pH was adjusted to 4-5 by adding citric acid aqueous solution (0.5 M), concentrated. The organic solvent was removed, filtered, and the filter cake was collected and dried under vacuum to obtain compound 1-7. $^1$HNMR (400 MHz, CDCl$_3$) δ ppm 8.31 (s, 1 H), 7.91-8.07 (m, 1 H), 7.57 (m, 1 H), 7.20-7.39 (m, 4 H), 6.44 (m, 1 H), 5.31 (s, 2 H), 5.02 (s, 2 H), 4.61-4.87 (m, 4 H), 4.44-4.60 (m, 1 H).

9) Synthesis of Compound 1-8b

Compound 1-8a (23.0 g, 159.59 mmol), tetrahydrofuran (460 mL) were added to a pre-dried reaction flask, and the reaction mixture was cooled down to -78° C. under nitrogen protection, then a mixed solution of 2 M lithium diisopropylamide in tetrahydrofuran and n-heptane (2 M, 119.69 mL) was added. After the reaction was carried out for 2 hours, a solution of ethyl cyanoformate (39.5 g, 398.98 mmol, 39.14 mL) in tetrahydrofuran (230 mL) was added to the reaction mixture, and the reaction was continued for 0.5 hours, then the reaction mixture was slowly warmed up to 15° C., and saturated ammonium chloride aqueous solution (700 mL) was added thereto. The mixture was extracted with ethyl acetate (700 mL*2), and the organic phases were combined and washed by adding saturated brine (300 mL), then the organic phase was collected, dried over anhydrous sodium sulfate, filtered, and the filtrate was concentrated under reduced pressure, then the crude product was purified by column chromatography (gradient elution: ethyl acetate/petroleum ether, ethyl acetate %: 0 to 100 %, flow rate of 20 mL/min) to obtain compound 1-8b. LCMS (ESI) m/z: 217[M+1]$^+$.

10) Synthesis of Compound 1-8c

Lithium borohydride (9.3 g, 427.42 mmol) and anhydrous tetrahydrofuran (220 mL) were added to a pre-dried three-necked flask under nitrogen protection, after the mixture was cooled down to 0° C., a mixed solution of compound 1-8b (220 g, 101.77 mmol) and anhydrous tetrahydrofuran (20 mL) was added thereto, then the mixture was naturally warmed up to 25° C., transferred to an oil bath of 40° C. and stirred for 17 hours. The combined system was quenched by slowly pouring into saturated ammonium chloride solution (1 L), and stirred slowly until no bubbles generated. Ethyl acetate (200 mL*3) was added for extraction, and the organic phases were collected, washed by adding saturated brine (100 mL), and the organic phase was dried over anhydrous sodium sulfate, filtered, and the filtrate was concentrated under reduced pressure to obtain compound 1-8c. LCMS (ESI) m/z: 157 [M-17]$^+$.

11) Synthesis of Compound 1-8d

Compound 1-8c (14.0 g, 80.39 mmol), N,N-dimethylformamide (140 mL), dichlorosulfoxide (44.0 g, 369.81 mmol, 26.83 mL) were added to a pre-dried single-necked flask, and the mixture was stirred at 25° C. for 0.5 hours, then the system was warmed up to 40° C., cooled down to 25° C. in an ice bath and the stirring was continued for 0.5 hours. The system was added with ethyl acetate (100 mL), washed with saturated sodium chloride aqueous solution (100 mL*3), and the organic phase was collected, dried by adding anhydrous sodium sulfate, filtered, and the filtrate was concentrated under reduced pressure to obtain compound 1-8d.

12) Synthesis of Compound 1-8

Compound 1-8d (15.4 g, 79.96 mmol), ammonia/methanol (14 M, 150 mL) were added to a pre-dried single-necked flask, and the mixture was stirred at 25° C. for 24 hours. The system was evaporated to dryness by rotary evaporation, and anhydrous dichloromethane (100 mL) was added, and the mixture was stirred at 25° C. for 0.5 hours, then filtered. The filter cake was rinsed with dichloromethane (10 mL*3), and the filtered solid was collected and concentrated under reduced pressure to obtain compound 1-8. $^1$HNMR (400 MHz, DMSO-d$_6$) δ ppm 7.28 (dt, J=5.4, 9.4 Hz, 1 H), 7.14 (dt, J=1.8, 9.2 Hz, 1 H), 4.03 (s, 2 H), 3.85 (s, 3 H); LCMS (ESI) m/z: 174[M+1]$^+$.

13) Synthesis of Compound 1

Compound 1-7 (50 mg, 130.42 μmol), compound 1-8 (22 mg, 130.42 μmol), N,N-dimethylformamide (2 mL), diisopropylethylamine (75 mg, 86.90 μmol) were added to a three-necked flask, then the mixture was cooled down to 0° C. HATU (2-(7-azobenzotriazole)-N,N,N,N-tetramethyluronium hexafluorophosphate) (74 mg, 194 μmol) was added thereto, and the mixture was stirred at 0° C. for 2 hours. The crude product was purified by preparative high performance liquid chromatography (chromatographic column: Welch Xtimate C18 150*25 mm*5 μm; mobile phase: A-10 mM ammonium bicarbonate aqueous solution; B-acetonitrile; B %: 30 %-50 %, 10.5 min) to obtain compound 1. $^1$HNMR (400 MHz, DMSO-d$_6$) δ ppm 8.25 (t, J=5.14 Hz, 1H), 8.21 (s, 1 H), 8.01-8.05 (m, 1 H), 7.56 (ddd, J=10.13, 7.12, 3.33 Hz, 1 H), 7.27-7.33 (m, 2 H), 7.20-7.26 (m, 2 H), 7.11 (td, J=9.35, 5.27 Hz, 1 H), 6.95-7.04 (m, 1 H), 6.43 (dd, J=10.04, 5.40 Hz, 1 H), 5.28 (s, 2 H), 5.01 (s, 2 H), 4.80 (dd, J=8.47, 5.58 Hz, 2H), 4.67 (t, J=6.27 Hz, 2 H), 4.46-4.56 (m, 1 H), 4.37 (d, J=4.89 Hz, 2 H), 3.81 (s, 3 H); LCMS (ESI) m/z: 539[M+1]$^+$.

Embodiment 2

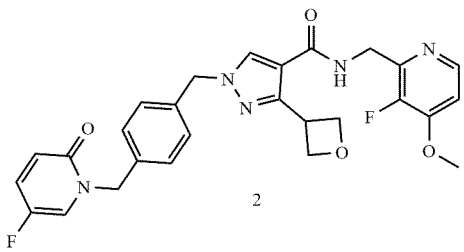

Synthetic route:

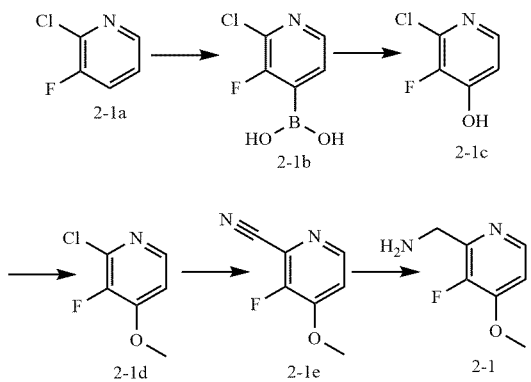

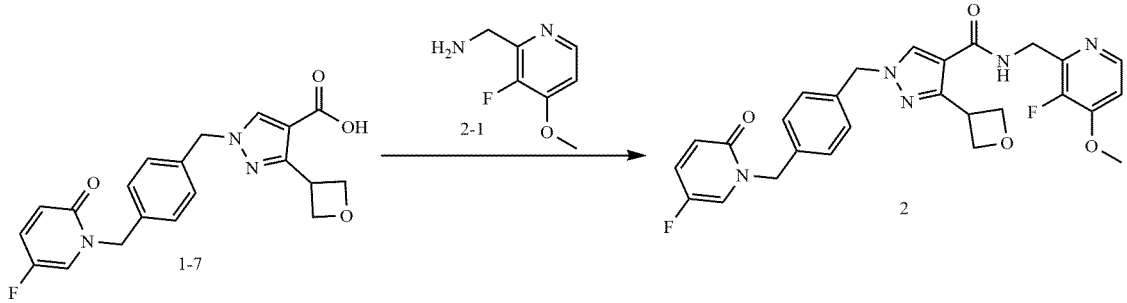

1) Synthesis of Compound 2-1b

Under nitrogen protection, a solution of compound 2-1a (25.0 g, 190.06 mmol) in tetrahydrofuran (200 mL) was added to a pre-dried three-necked flask, and the mixture was cooled down to -78° C., and a mixed solution of 2 M lithium diisopropylamide in tetrahydrofuran and n-heptane (2 M, 104.53 mL) was added dropwise, and the mixture was stirred for 2 hours. The raw material trimethyl borate (39.5 g, 380.13 mmol, 42.93 mL) was added dropwise, and the temperature was naturally warmed up to room temperature of 25° C. and the stirring was continued for 22 hours. Saturated ammonium chloride aqueous solution (200 mL) was added to the mixture to quench the system, and ethyl acetate (200 mL) was added and the mixture was stirred for 30 minutes. The aqueous phase was separated and collected, then concentrated under reduced pressure to obtain the crude product of 2-1b.

2) Synthesis of Compound 2-1c

At 0 to 5° C., hydrogen peroxide (59.0 g, 520.36 mmol, 50 mL, 30 % purity) was added dropwise to a solution of compound 2-1b (33.3 g, 189.90 mmol) in ethanol (330 mL), then the resulting mixture was naturally warmed up to room temperature of 25° C. and stirred for 4.5 hours. Additional hydrogen peroxide (118.0 g, 1.04 mol, 100 mL, 30 % purity) was added thereto and the stirring was continued for 18 hours. The reaction system was added with saturated sodium sulfite aqueous solution (500 mL), and stirred for 1 hour until the starch potassium iodide test paper did not change color, then the mixture was extracted with ethyl acetate (300 mL*3). The organic phases were collected and combined, dried by adding anhydrous sodium sulfate, filtered, and the filtrate was concentrated under reduced pressure to obtain compound 2-1c. LCMS (ESI) m/z: 148[M+1]$^+$.

3) Synthesis of Compound 2-1d

Compound 2-1c (7.9 g, 53.41 mmol), N,N-dimethylformamide (80 mL), potassium carbonate (14.8 g, 106.82 mmol) and iodomethane (11.4 g, 80.12 mmol, 4.99 mL) were added to a pre-dried single-necked flask, and the mixture was stirred at 25° C. for 18 hours. The system was added with ethyl acetate (30 mL) and stirred for 10 min, then the system was filtered through a Buchner funnel. The filter cake was rinsed with ethyl acetate (15 mL*3), then the filtrate was collected and washed by adding saturated brine (40 mL*3), and the organic phase was separated, dried by adding anhydrous sodium sulfate, filtered, and the filtrate was concentrated under reduced pressure, and the crude product was purified by column chromatography (gradient elution: ethyl acetate/petroleum ether, ethyl acetate %: 0 to 30 %, flow rate: 30 mL/min) to obtain the compound 2-1d. LCMS (ESI) m/z: 162[M+1]$^+$.

4) Synthesis of Compound 2-1e

Compound 2-1d (2.9 g, 17.95 mmol), N,N-dimethylformamide (30 mL), zinc cyanide (2.1 g, 17.95 mmol, 1.14 mL), 1,1-bis(diphenylphosphino)ferrocene (995 mg, 1.79 mmol), tris(dibenzylideneacetone)dipalladium (822 mg, 897.49 μmol) were added to a pre-dried single-necked flask, and the mixture was purged with nitrogen for three times and stirred at 120° C. for 16 hours. The system was filtered, and the filter cake was rinsed with ethyl acetate (30 mL*5). Saturated brine was added to the filtrate, and the mixture was stirred for 20 min, and separated by a separatory funnel, and the organic phase was dried by adding anhydrous sodium sulfate, filtered, and the filtrate was concentrated under reduced pressure, and the crude product was purified by column chromatography (gradient elution: ethyl acetate/petroleum ether, ethyl acetate %: 0 to 50 %, flow rate of 30 mL/min) to obtain compound 2-1e. LCMS (ESI) m/z: 153[M+1]$^+$.

5) Synthesis of Compound 2-1

Compound 2-1e (1.8 g, 11.83 mmol), anhydrous ethanol (10 mL), anhydrous tetrahydrofuran (10 mL), hydrochloric acid (1.20 g, 11.83 mmol, 1.17 mL, 36 % purity), palladium/carbon (500 mg, 10 % purity) were added to a pre-dried single-necked flask, and hydrogen gas (23.85 mg, 11.83 mmol) was bubbled at 15 psi, then the mixture was stirred at 25° C. for 4 hours. The system was filtered through diatomite, and the filter cake was rinsed with methanol (20 mL*4) until no product remained, then the filtrate was concentrated under reduced pressure to obtain compound 2-1. $^1$HNMR (400 MHz, DMSO-d$_6$) δ ppm 8.36 (d, J=5.6 Hz, 1H), 7.34 (t, J=6.2 Hz, 1H), 4.20 - 4.15 (m, 2H), 3.96 (s, 3H), LCMS (ESI) m/z: 156[M+1]$^+$.

6) Synthesis of Compound 2

N,N-Dimethylformamide (1 mL), compound 1-7 (50 mg, 130.42 μmol), compound 2-1 (28 mg, 143.46 μmol), and N,N-diisopropylethylamine (135 mg, 1.04 mmol) were added to a pre-dried reaction flask at 0° C. Then, HATU (74 mg, 194 μmol) was added, and the mixture was stirred at 20° C. for 2 hours. The system was filtered, and the crude product was purified by preparative high performance liquid chromatography (chromatographic column: Welch Xtimate C18 150*25 mm*5 μm; mobile phase: A-10 mM ammonium bicarbonate aqueous solution; B-acetonitrile; B %: 25 %-55 %, 10.5 min) to obtain compound 2. $^1$HNMR (400 MHz, CD$_3$OD) δ ppm 8.16 (d, J=5.6 Hz, 1 H), 8.10 (s, 1 H), 7.77 (t, J=3.8 Hz, 1 H), 7.54 (m, 1 H), 7.25-7.37 (m, 4 H), 7.11 (t, J=6.2 Hz, 1 H), 6.57 (dd, J=5.2, 10.0 Hz, 1 H), 5.32 (s, 2 H), 5.14 (s, 2 H), 4.93-5.02 (m, 2 H), 4.88-4.92 (m, 2 H), 4.60-4.70 (m, 1 H), 4.57 (d, J=2.0 Hz, 2 H), 3.95 (s, 3 H).

Embodiment 3

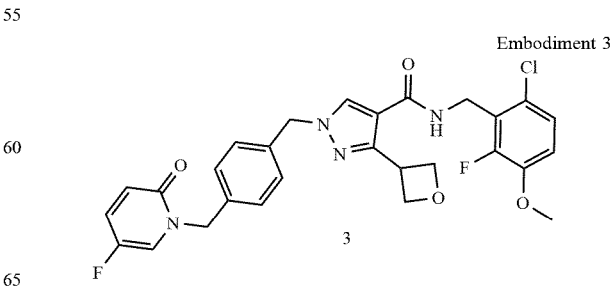

Synthetic route:

17

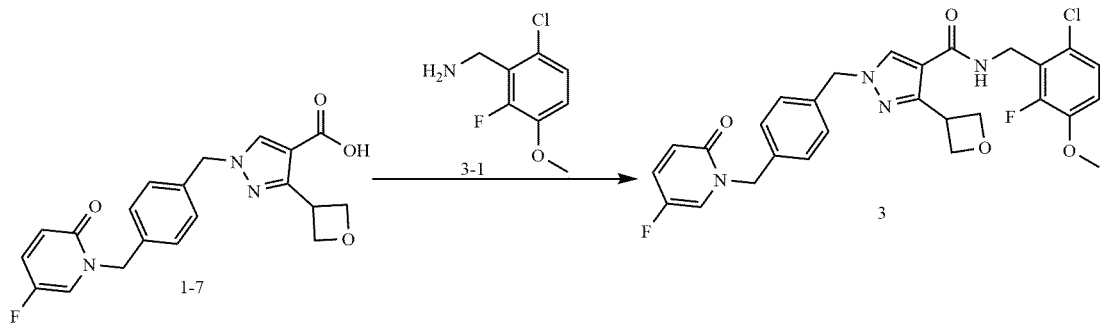

Synthesis of Compound 3

N,N-Dimethylformamide (1 mL), compound 1-7 (50 mg, 130.42 μmol), compound 3-1 (30 mg, 156.51 μmol), and N,N-diisopropylethylamine (76 mg, 586.90 μmol) were added to a pre-dried reaction flask at 0° C., then HATU (74 mg, 194 μmol) was added thereto, and the mixture was stirred at 25° C. for 2 hours. The system was filtered, and the crude product was purified by preparative high performance liquid chromatography (chromatographic column: Welch Xtimate C18 150*25 mm*5 μm; mobile phase: A-10 mM ammonium bicarbonate aqueous solution; B-acetonitrile; B %: 30 %-60 %, 10.5 min) to obtain compound 3. ¹HNMR (400 MHz, CDCl₃) δ ppm 8.21 (s, 1 H), 8.10-8.18 (m, 1H), 7.97-8.08 (m, 1 H), 7.56 (m, 1 H), 7.27-7.33 (m, 2 H), 7.20-7.26 (m, 3 H), 7.10-7.18 (m, 1 H), 6.43 (dd, J=5.4, 10.0 Hz, 1 H), 5.28 (s, 2 H), 5.01 (s, 2 H), 4.80 (dd, J=5.6, 8.6 Hz, 2 H), 4.64-4.71 (m, 2 H), 4.48-4.59 (m, 1 H), 4.43 (m, 2 H), 3.81-3.86 (m, 3 H); LCMS (ESI) m/z: 555[M+1]⁺.

Embodiment 4

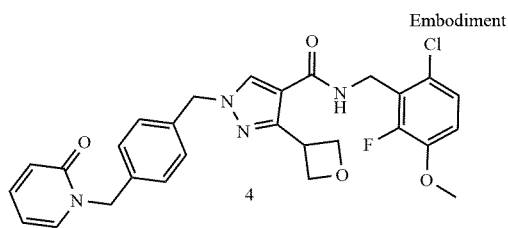

Synthetic route:

18

1) Synthesis of Compound 4-2

Potassium carbonate (4.6 g, 33.64 mmol) was added to a solution of compound 1-5 (3.1 g, 15.80 mmol) and compound 4-1 (3.7 g, 15.96 mmol) in N,N-dimethylformamide (50 mL), and the resulting mixture was heated to 65° C. and stirred for 4 hours. Ethyl acetate (100 mL) and water (50 mL) were added to the reaction mixture and the mixture was stirred for 10 minutes, then the aqueous phase was removed, and the organic phase was concentrated under reduced pressure, and the residue was added with ethyl acetate (6 mL), stirred for 10 minutes, and filtered to obtain 4-2. ¹HNMR (400 MHz, CDCl₃) δ ppm 7.80 (s, 1 H), 7.25-7.37 (m, 6 H), 6.62 (d, J=8.0 Hz, 1 H), 6.17 (td, J=6.8, 1.3 Hz, 1H), 5.30 (s, 1 H), 5.25 (s, 2 H), 5.15 (s, 2 H), 4.93-5.06 (m, 4 H), 4.63 (t, J=7.8 Hz, 1 H), 4.22 (q, J=7.2 Hz, 2 H), 1.31 (t, J=7.2 Hz, 3 H).

2) Synthesis of Compound 4-3

Sodium hydroxide aqueous solution (2.5 M, 18.91 mL) was added to a solution of compound 4-2 (6.2 g, 15.76 mmol) in ethanol (70 mL), and the resulting mixture was heated to 35° C. and stirred for 16 hours. 0.5 M citric acid aqueous solution was added dropwise to the reaction mixture to adjusted the pH to 4-5, then a large amount of white solid was precipitated, and the solid was collected by filtration. Ethanol (30 mL) was added and the mixture was stirred for 10 min, and compound 4-3 was obtained by filtration. ¹HNMR (400 MHz, CDCl₃) δ ppm 7.84 (s, 1 H), 7.23-7.38 (m, 6 H), 6.66 (d, J=8.8 Hz, 1 H), 6.16-6.23 (m, 1 H), 5.27 (s, 2 H), 5.16 (s, 2 H), 4.94-5.07 (m, 4 H), 4.64 (t, J=7.7 Hz, 1 H).

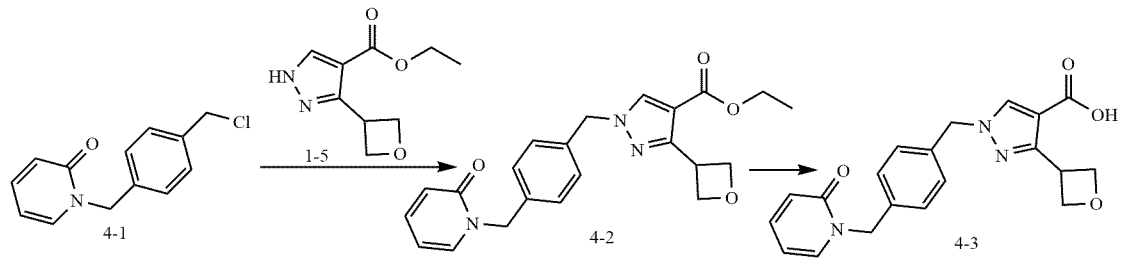

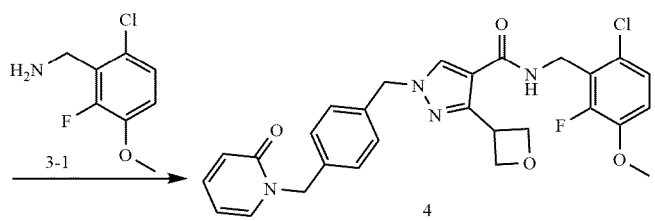

3) Synthesis of Compound 4

Compound 4-3 (50 mg, 136.84 μmol), compound 3-1 (25 mg, 136.84 μmol), N,N-dimethylformamide (2 mL), diisopropylethylamine (79 mg, 615.78 μmol) were added to a three-necked flask, then the mixture was cooled down to 0° C., and HATU (78 mg, 205.26 μmol) was added thereto, and the mixture was stirred at 0° C. for 2 hours. The crude product was purified by preparative high performance liquid chromatography (chromatographic column: Welch Xtimate C18 150*25 mm*5 μm; mobile phase: A-10 mM ammonium bicarbonate aqueous solution; B-acetonitrile; B %: 40 %-70 %, 10.5 min) to obtain compound 4. ¹HNMR (DMSO-$d_6$, 400 MHz) δ ppm 8.20 (s, 1 H), 8.08-8.14 (m, 1 H), 7.72-7.78 (m, 1 H), 7.37-7.44 (m, 1 H), 7.11-7.30 (m, 6 H), 6.39 (d, J=9.16 Hz, 1 H), 6.17-6.25 (m, 1 H), 5.27 (s, 2 H), 5.06 (s, 2 H), 4.80 (dd, J=8.41, 5.52 Hz, 2 H), 4.68 (t, J=6.27 Hz, 2 H), 4.48-4.59 (m, 1 H), 4.43 (br d, J=3.26 Hz, 2 H), 3.84 (s, 3 H); LCMS (ESI) m/z: 537 [M+1]⁺.

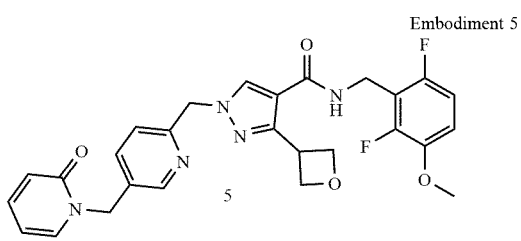

Embodiment 5

Synthetic route:

1) Synthesis of Compound 5-2

Compound 5-1 (3.0 g, 13.44 mmol), anhydrous calcium chloride (6.0 g, 53.76 mmol), anhydrous ethanol (33 mL), anhydrous tetrahydrofuran (35 mL) were added to a pre-dried reaction flask. The mixture was cooled down to 0° C., and sodium borohydride (1.0 g, 26.88 mmol) was added thereto and the mixture was stirred at 0° C. for 5 hours. Saturated ammonium chloride solution (150 mL) was added to the reaction flask and the mixture was stirred for 10 minutes. The temperature was naturally warmed up to 27° C., and dichloromethane (250 mL) and water (250 mL) were added to the reaction flask, and the mixture was extracted and the phases were separated, and the organic phase was collected. Dichloromethane (250 mL) was added to the aqueous phase, extracted and the phases were separated, then the organic phase was dried over anhydrous sodium sulfate, filtered, and concentrated under reduced pressure. Compound 5-2 was obtained. LCMS (ESI) m/z: 182[M+1]⁺.

2) Synthesis of Compound 5-3

Compound 5-2 (2.2 g, 12.14 mmol) and anhydrous dichloromethane (25 mL) were added to a pre-dried reaction flask, and the mixture was cooled down to 0° C., then sulfoxide chloride (7.7 g, 64.35 mmol, 4.67 mL) was added at 0° C. The mixture was naturally warmed up to 27° C. and stirred for 3 hours. Saturated sodium bicarbonate solution (100 mL) was added to the reaction mixture, then dichloromethane (200 mL) was added, and the mixture was extracted and the phases were separated, and the organic phase was collected.

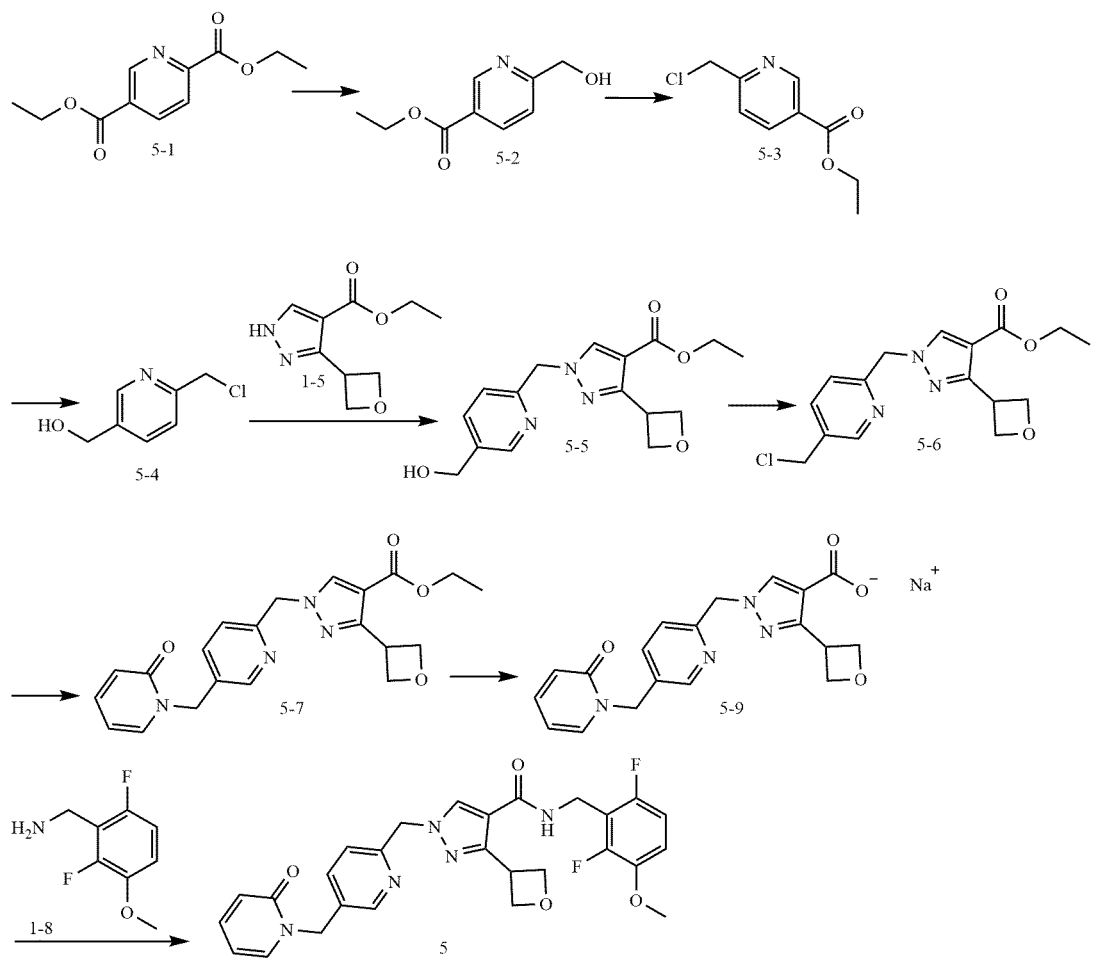

Dichloromethane (200 mL) was added to the aqueous phase, then the organic phases were collected, combined, dried over anhydrous sodium sulfate, filtered, and concentrated under reduced pressure to obtain compound 5-3. $^1$HNMR (400 MHz, CDCl$_3$) δ ppm 9.11 (d, J=1.62 Hz, 1 H), 8.28 (dd, J=8.08, 2.06 Hz, 1 H), 7.54 (d, J=8.16 Hz, 1 H), 4.62-4.75 (m, 2 H), 4.31-4.45 (m, 2 H), 1.29-1.45 (m, 3 H); LCMS (ESI) m/z: 200[M+1]$^+$.

3) Synthesis of Compound 5-4

Compound 5-3 (1.7 g, 8.47 mmol), anhydrous tetrahydrofuran (20 mL) were added to a pre-dried reaction flask at 27° C., then the mixture was cooled down to -78° C., and then diisobutylaluminum hydride (1 M, 29.63 mL) was added thereto, and the mixture was maintained at -78° C. and stirred for 3 hours. Sodium hydroxide solution (30 mL) was added and the mixture was stirred for 5 minutes. The mixture was filtered through diatomite, and the filtrate was collected. Ethyl acetate (50 mL) was added to the filtrate, and the mixture was extracted and the phases were separated, and the organic phase was collected. The organic phase was dried over anhydrous sodium sulfate, filtered and concentrated under reduced pressure. The crude product was purified by column chromatography to obtain compound 5-4. LCMS (ESI) m/z: 158[M+1]$^+$.

4) Synthesis of Compound 5-5

Compound 5-4 (600 mg, 3.68 mmol), 1-5 (737 mg, 3.75 mmol), N,N-dimethylformamide (6 mL) and anhydrous potassium carbonate (1.1 g, 8.10 mmol) were added to a pre-dried single-necked flask, and the mixture was stirred at 65° C. for 12 hours. The temperature was naturally cooled down to 27° C., and dichloromethane (20 mL) was added to the reaction flask. The mixture was stirred for 10 minutes, then filtered, and the filtrate was concentrated under reduced pressure. The residue was purified by column chromatography to obtain compound 5-5. LCMS (ESI) m/z: 318[M+1]$^+$.

5) Synthesis of Compound 5-6

Compound 5-5 (300 mg, 945.36 µmol), anhydrous dichloromethane (4 mL) and triethylamine (383 mg, 3.78 mmol, 526.33 µL) were added to a pre-dried reaction flask, and methylsulfonyl chloride (161 mg, 1.40 mmol, 108.59 µL) was added at 0° C., then the mixture was naturally warmed up to 27° C. and stirred for 7 hours. Water (50 mL) was added to the reaction mixture and the mixture was stirred for 10 min, and the aqueous phase was removed by extraction and phase separation, then the organic phase was obtained, dried over anhydrous sodium sulfate, filtered under reduced pressure and concentrated under reduced pressure. Compound 5-6 was obtained. LCMS (ESI) m/z: 336[M+1]$^+$.

6) Synthesis of Compound 5-7

Compound 5-6 (300 mg, 744.52 µmol), 2-hydroxypyridine (74 mg, 781.75 µmol), N,N-dimethylformamide (3 mL) and anhydrous potassium carbonate (103 mg, 744.52 µmol) were added to a pre-dried reaction flask. The reaction was heated to 70° C. and carried out for 12 hours. Then the mixture was naturally cooled down to 27° C., and then N,N-dimethylformamide (2 mL) was added. The mixture was filtered, and the filtrate was concentrated under reduced pressure, then purified by preparative high performance liquid chromatography (neutral system) to obtain compound 5-7. LCMS (ESI) m/z: 395[M+1]$^+$.

7) Synthesis of Compound 5-9

Compound 5-7 (54 mg, 136.91 µmol), sodium hydroxide (16 mg, 410.73 µmol), anhydrous ethanol (1 mL), anhydrous tetrahydrofuran (1 mL), water (0.3 mL) were added to a pre-dried reaction flask, and the mixture was stirred at 75° C. for 20 hours. The system was concentrated to dryness under reduced pressure to obtain the crude product of compound 5-9. LCMS (ESI) m/z: 366 [M-22]$^+$.

8) Synthesis of Compound 5

Compound 1-9 (44 mg, 120.10 µmol), 1-8 (21 mg, 120.10 µmol), N,N-diisopropylethylamine (70 mg, 540.44 µmol, 94.13 µL), N,N-dimethylformamide (0.6 mL) were added to a pre-dried three-necked flask, then the mixture was cooled down to 0° C., and HATU (69 mg, 180.15 µmol) was added thereto, and the mixture was stirred at 0° C. for 3 hours. The reaction system was filtered, and the filtrate was purified by preparative high performance liquid chromatography (chromatographic column: Welch Xtimate C18 150*25 mm*5 µm; mobile phase: A-10 mM ammonium bicarbonate aqueous solution; B-acetonitrile B %: 20 %-50 %, 10.5 min) to obtain compound 5. $^1$HNMR (400 MHz, CDCl$_3$) δ ppm 8.55 (d, J=1.8 Hz, 1 H), 7.76 (s, 1 H), 7.66 (dd, J=2.2, 8.0 Hz, 1 H), 7.37-7.28 (m, 2 H), 7.15 (d, J=8.2 Hz, 1 H), 6.91-6.78 (m, 2 H), 6.61 (d, J=9.2 Hz, 1 H), 6.20 (t, J=6.2 Hz, 1 H), 6.02 (br s, 1 H), 5.36 (s, 2 H), 5.13 (s, 2 H), 5.03 (dd, J=5.8, 8.6 Hz, 2 H), 4.92 (t, J=6.2 Hz, 2 H), 4.67-4.61 (m, 3 H), 3.87 (s, 3 H).

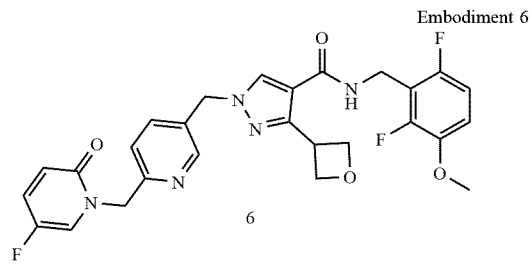

Embodiment 6

Synthetic route:

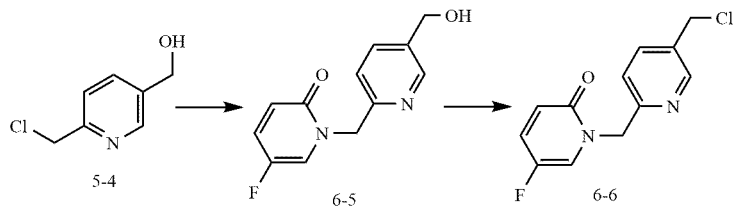

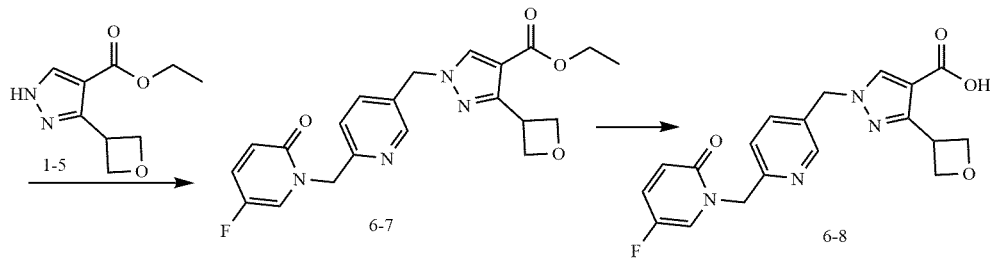

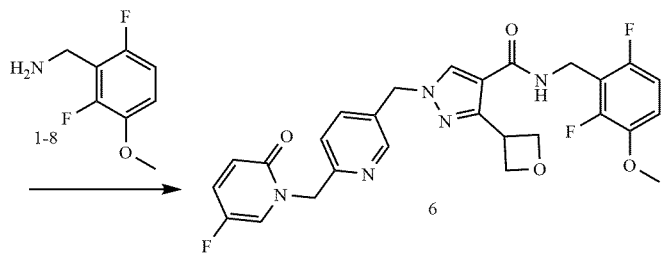

1) Synthesis of Compound 6-5

Compound 5-4 (0.5 g, 3.49 mmol), 5-fluoro-2-hydroxypyridine (414 mg, 3.66 mmol), acetonitrile (6 mL), anhydrous potassium carbonate (482 mg, 3.49 mmol) were added to a pre-dried reaction flask. The mixture was warmed up to 65° C. and stirred for 12 hours. The temperature was naturally cooled down to 27° C., and dichloromethane (50 mL) was added to the reaction flask. The mixture was stirred for 10 minutes, filtered, and the filtrate was concentrated under reduced pressure to obtain compound 6-5. $^1$HNMR (400 MHz, CDCl$_3$) δ ppm 8.55 (s, 1 H), 7.35-7.53 (m, 5 H), 6.50-6.69 (m, 5 H), 5.18 (s, 2 H), 4.70-4.76 (m, 2 H). 3.51 (s, 1 H); LCMS (ESI) m/z: 235 [M+1]$^+$.

2) Synthesis of Compound 6-6

Compound 6-5 (0.1 g, 426.9 μmol), dichloromethane (1.5 mL) were added to a pre-dried reaction flask, and the mixture was cooled down to 0° C., and sulfoxide chloride (253 mg, 2.13 mmol, 154.8 μL) was added thereto at 0° C. The reaction was naturally warmed up to 27° C. and carried out for 3 hours. The reaction system was quenched by pouring into saturated sodium bicarbonate solution (20 mL), stand for 5 minutes, then dichloromethane (10 mL) and water (10 mL) were added, and the mixture was extracted and the phases were separated, and the organic phase was collected. Dichloromethane (10 mL) was added to the aqueous phase, and the mixture was extracted and the phases were separated, then the organic phases were combined. The organic phase was dried over anhydrous sodium sulfate, filtered and concentrated under reduced pressure to obtain compound 6-6. $^1$HNMR (400 MHz, CDCl$_3$) δ ppm 8.57 (d, J=1.75 Hz, 1 H), 7.73 (dd, J=7.89, 2.19 Hz, 1 H), 7.41-7.49 (m, 2 H), 7.28-7.33 (m, 1 H), 6.57 (dd, J=10.09, 5.26 Hz, 1 H), 5.18 (s, 2 H), 4.58 (s, 2 H); LCMS (ESI) m/z: 253 [M+1]$^+$.

3) Synthesis of Compound 6-7

Compound 6-6 (0.1 g, 395.7 μmol), compound 1-5 (78 mg, 399.3 μmol), anhydrous potassium carbonate (116 mg, 842.9 μmol), N,N-dimethylformamide (2 mL) were added to a pre-dried thumb bottle at 25° C. The mixture was heated to 65° C. in an oil bath and stirred for 12 hours. The temperature was naturally cooled down to 27° C., then dichloromethane (20 mL) and water (20 mL) were added to the reaction flask, and the mixture was extracted and the phases were separated, and the organic phase was collected. Dichloromethane (20 mL) was added to the aqueous phase, and the mixture was extracted and the phases were separated, then the organic phases were combined. The organic phase was dried over anhydrous sodium sulfate, filtered and concentrated under reduced pressure to obtain compound 6-7. $^1$HNMR (400 MHz, CDCl$_3$) δ ppm 8.38-8.58 (m, 1 H), 7.78-8.08 (m, 1 H), 7.49-7.67 (m, 1 H), 5.12-5.35 (m, 2 H), 4.78-5.06 (m, 2 H), 4.12-4.38 (m, 1 H), 3.51 (s, 2 H), 1.22-1.38 (m, 3 H); LCMS (ESI) m/z: 413 [M+1]$^+$.

4) Synthesis of Compound 6-8

Compound 6-7 (0.1 g, 193.9 μmol) was added to a pre-dried reaction flask at 27° C. and dissolved in anhydrous tetrahydrofuran (2 mL), then sodium hydroxide solution (2 M, 387.9 μL) and ethanol (2 mL) were added to the system. The mixture was warmed up to 40° C. and stirred for 12 hours. Then the reaction was naturally cooled down to 27° C., and hydrochloric acid (1 M, 10 mL) was added to the reaction flask to adjust the pH of the solution to 6. Dichloromethane (10 mL) and water (10 mL) were added to the reaction flask, and the mixture was extracted and the phases were separated, and the organic phase was collected. Dichloromethane (10 mL) was added to the aqueous phase, and the mixture was extracted and the phases were separated, then the organic phases were combined, dried over anhydrous sodium sulfate, filtered, and concentrated under reduced pressure to obtain compound 6-8. LCMS (ESI) m/z: 385[M+1]$^+$.

5) Synthesis of Compound 6

Compound 6-8 (36 mg, 93.6 μmol), compound 1-8 (16 mg, 93.6 μmol), N,N-diisopropylethylamine (54 mg, 421.8 μmol, 73.4 μL), N,N-dimethylformamide (1 mL) were added to a pre-dried single-necked flask at 27° C., then the mixture was cooled down to 0° C., and HATU (53 mg, 140.5 μmol) was added thereto, and the mixture was stirred at 0° C. for 5 hours. The reaction was naturally warmed up to 27° C., and then water (10 mL) and ethyl acetate (20 mL) were added, and the mixture was extracted and the phases were separated, then the organic phase was collected and concentrated under reduced pressure to obtain the crude product, and the crude product was purified by preparative high performance liquid chromatography (chromatographic column: Welch Xtimate C18 150*25 mm*5 μm; mobile phase: A-10 mM ammonium bicarbonate aqueous solution; B-acetonitrile; B %: 25 %-55 %, 10.5 min) to obtain compound 6. $^{1}$HNMR (400 MHz, DMSO-d$_{6}$) δ ppm 8.37-8.51 (m, 1 H), 7.34-7.63 (m, 5 H), 6.84 (d, J=8.33 Hz, 1 H), 5.16 (s, 2 H), 5.04 (dd, J=8.33, 6.14 Hz, 2 H), 4.88-4.94 (m, 2 H), 4.64 (d, J=5.26 Hz, 2 H), 3.86 (s, 2 H), 3.54 (s, 6 H); LCMS (ESI) m/z: 541 [M+1]$^{+}$.

Embodiment 7

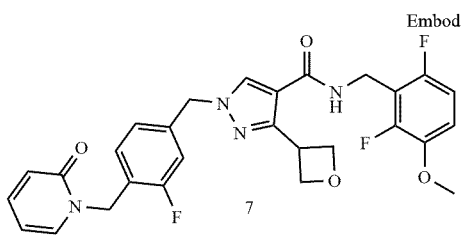

Synthetic route:

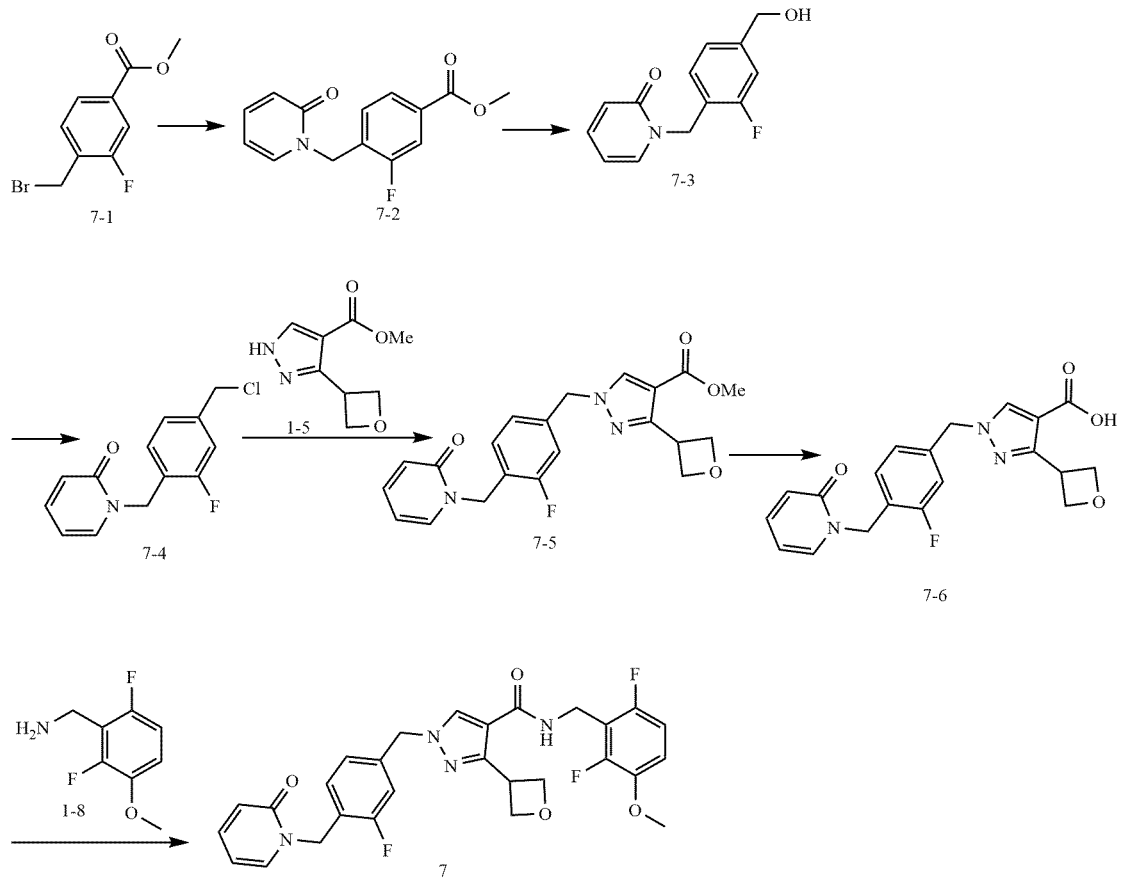

1) Synthesis of Compound 7-2

N,N-Dimethylformamide (40 mL), anhydrous potassium carbonate (3.4 g, 24.29 mmol), compound 7-1 (4 g, 16.19 mmol), 2-hydroxypyridine (1.6 g, 17.00 mmol) were added to a pre-dried three-necked flask. The mixture was heated and stirred at 70° C. for 4 hours, diluted with ethyl acetate (150 mL) and water (300 mL), and the organic phase was collected after the phases were separated, and the aqueous phase was extracted with ethyl acetate (100 mL). The organic phases were combined, washed with saturated brine (200 mL), dried over anhydrous sodium sulfate, filtered, and concentrated under reduced pressure to obtain the crude product, and the crude product was purified by column chromatography to obtain compound 7-2. $^{1}$HNMR (400 MHz, CDCl$_{3}$) δ ppm 7.79 (dd, J=7.89, 1.75 Hz, 1 H), 7.73 (dd, J=10.52, 1.32 Hz, 1 H), 7.48 (t, J=7.67 Hz, 1 H), 7.31-7.40 (m, 2 H), 6.60 (d, J=9.21 Hz, 1 H), 6.19 (td, J=6.80, 1.32 Hz, 1 H), 5.21 (s, 2 H), 3.92 (s, 3 H); LCMS (ESI) m/z: 162 [M+1]$^{+}$.

2) Synthesis of Compound 7-3

Compound 7-2 (2.3 g, 8.82 mmol), anhydrous tetrahydrofuran (30 mL) were added to a pre-dried reaction flask. Lithium borohydride (2 M, 22.06 mL) was added to the reaction flask at 0° C. in an ice bath, and the mixture was naturally warmed up to 27° C. and stirred for 12 hours. The reaction system was cooled down to 0° C., diluted by adding ethyl acetate (50 mL) and water (50 mL), and the organic phase was collected after the phases were separated, and the aqueous phase was extracted with ethyl acetate (50 mL). The organic phases were combined, washed with saturated brine (50 mL), dried over anhydrous sodium sulfate, filtered, and concentrated under reduced pressure to obtain the crude product, and the crude product was purified by column chromatography to obtain compound 7-3. $^1$HNMR (400 MHz, CDCl$_3$) δ ppm 7.35-7.46 (m, 2H), 7.27-7.35 (m, 1H), 7.04-7.16 (m, 2H), 6.56 (d, J=9.21 Hz, 1H), 6.16 (td, J=6.80, 1.32 Hz, 1H), 5.13 (s, 2H), 4.60 - 4.74 (m, 2H); LCMS (ESI) m/z: 234 [M+1]$^+$.

3) Synthesis of Compound 7-4

Compound 7-3 (1.8 g, 7.72 mmol), dichloromethane (20 mL) and triethylamine (1.6 g, 15.43 mmol, 2.2 mL) were added to a pre-dried reaction flask at 27° C., and methylsulfonyl chloride (1.1 g, 9.26 mmol, 716.8 μL) was added thereto at 0° C., then the mixture was naturally warmed up to 27° C. and stirred for 12 hours. Water (100 mL) was added to the reaction mixture and the mixture was stirred for 10 min, then the aqueous phase was removed by extraction and phase separation, and the organic phase was obtained, and concentrated under reduced pressure to obtain the crude product, then the crude product was purified by column chromatography to obtain compound 7-4. LCMS (ESI) m/z: 252 [M+1]$^+$.

4) Synthesis of Compound 7-5

Compound 7-4 (0.2 g, 794.7 μmol), 1-5 (157 mg, 802.6 μmol), anhydrous potassium carbonate (234 mg, 1.69 mmol), N,N-dimethylformamide (3 mL) were added to a pre-dried thumb bottle at 25° C. The mixture was heated to 65° C. in an oil bath and stirred for 12 hours. The reaction system was cooled down to 0° C., diluted by adding ethyl acetate (50 mL) and water (30 mL), and the organic phase was collected after the phases were separated, and the aqueous phase was extracted with ethyl acetate (30 mL). The organic phases were combined, washed twice with saturated brine (10 mL), dried over anhydrous sodium sulfate, filtered, and concentrated under reduced pressure to obtain the crude product, and the crude product was purified by column chromatography to obtain compound 7-5. LCMS (ESI) m/z: 412 [M+1]$^+$.

5) Synthesis of Compound 7-6

Compound 7-5 (0.2 g, 529.8 μmol) was added to a pre-dried reaction flask at 27° C. and dissolved in anhydrous tetrahydrofuran (3 mL), then sodium hydroxide solution (2 M, 1.1 mL) and ethanol (4 mL) were added to the system, and the mixture was warmed up to 40° C. and stirred for 6 hours. The reaction was naturally cooled down to 27° C., then hydrochloric acid (1 M, 10 mL) was added, and the pH of the reaction mixture was adjusted to 1. Dichloromethane (10 mL) and water (10 mL) were added, and the mixture was extracted and the phases were separated, and the organic phase was collected. Dichloromethane (20 mL) was added to the aqueous phase again, and the mixture was extracted and the phases were separated, then the organic phases were combined. The organic phase was dried over anhydrous sodium sulfate, filtered and concentrated under reduced pressure to obtain compound 7-6. $^1$HNMR (400 MHz, CDCl$_3$) δ ppm 7.48 (t, J=7.84 Hz, 1 H), 7.40 (br d, J=7.03 Hz, 1 H), 7.30-7.37 (m, 1 H), 6.93-7.07 (m, 2 H), 6.61 (d, J=8.78 Hz, 1 H), 5.22-5.33 (m, 2 H), 5.16 (s, 2 H), 5.00-5.07 (m, 2 H), 4.91-5.00 (m, 2 H), 4.65 (t, J=7.65 Hz, 1H); LCMS (ESI) m/z: 384 [M+1]$^+$.

6) Synthesis of Compound 7

Compound 1-8 (22 mg, 130.4 μmol), compound 7-6 (0.1 g, 130.4 μmol), N,N-diisopropylethylamine (75 mg, 586.9 μmol, 102.2 μL), N,N-dimethylformamide (2 mL) were added to a pre-dried single-necked flask at 27° C., then the mixture was cooled down to 0° C., and HATU (74 mg, 194 μmol) was added, and the mixture was stirred at 0° C. for 6 hours. The reaction was naturally warmed up to 27° C., then water (10 mL) and ethyl acetate (20 mL) were added, and the mixture was extracted and the phases were separated, then the organic phase was collected. The organic phase was dried over anhydrous sodium sulfate, filtered, and concentrated under reduced pressure to obtain the crude product, and the crude product was purified by preparative high performance liquid chromatography (chromatographic column: Welch Xtimate C18 150*25 mm*5 μm; mobile phase: A-10 mM ammonium bicarbonate aqueous solution; B-acetonitrile; B %: 30 %-50 %, 10.5 min) to obtain compound 7. $^1$HNMR (400 MHz, CDCl$_3$) δ ppm 7.60 (s, 1 H), 7.29-7.46 (m, 3 H), 6.90-7.02 (m, 2 H), 6.78-6.89 (m, 2 H), 6.57 (d, J=9.21 Hz, 1 H), 6.13-6.22 (m, 1 H), 6.06 (br s, 1 H), 5.22 (s, 2 H), 5.13 (s, 2 H), 5.04 (dd, J=8.33, 5.70 Hz, 2 H), 4.93 (t, J=6.36 Hz, 2 H), 4.58-4.68 (m, 3 H), 3.86 (s, 3H); LCMS (ESI) m/z: 539 [M+1]$^+$.

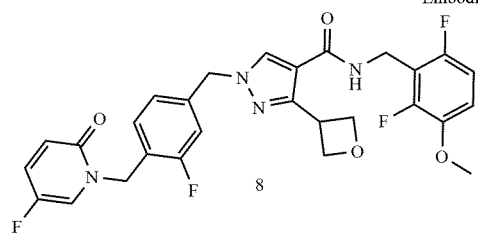

Embodiment 8

Synthetic route:

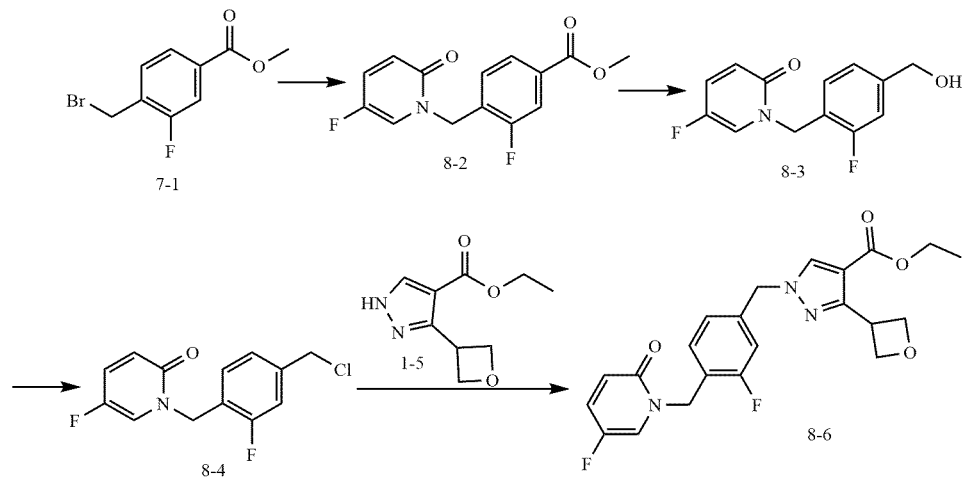

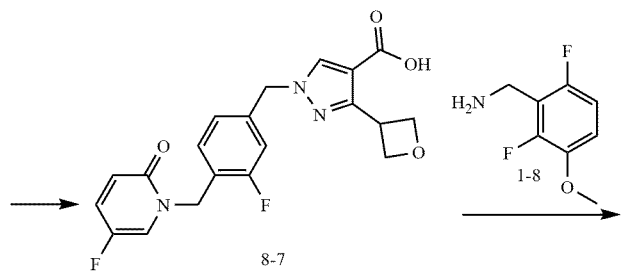
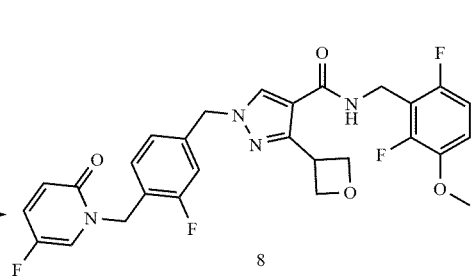

1) Synthesis of Compound 8-2

Compound 7-1 (1 g, 4.05 mmol), 5-fluoro-2-hydroxypyridine (503 mg, 4.45 mmol), potassium carbonate (1.1 g, 8.50 mmol), N,N-dimethylformamide (15 mL) were added to a pre-dried single-necked flask, and the mixture was stirred at 65° C. for 20 hours. The system was filtered, and the filter cake was rinsed with ethyl acetate (15 mL*3), then the filtrate was collected and washed with water (30 mL*3), then the organic phase was separated and dried by adding anhydrous sodium sulfate, filtered, and the filtrate was concentrated to dryness under reduced pressure, and the crude product was purified by column chromatography to obtain compound 8-2. $^1$HNMR (400 MHz, CD$_3$OD) δ ppm 7.84-7.78 (m, 2 H), 7.73 (dd, J=1.4, 10.7 Hz, 1 H), 7.59 (ddd, J=3.2, 7.0, 10.1 Hz, 1 H), 7.35 (t, J=7.8 Hz, 1 H), 6.58 (dd, J=5.0, 10.0 Hz, 1 H), 5.25 (s, 2 H), 3.90 (s, 3 H).

2) Synthesis of Compound 8-3

Compound 8-2 (523 mg, 1.87 mmol), anhydrous tetrahydrofuran (2 mL) were added to a pre-dried single-necked flask, and lithium borohydride (285.6 mg, 13.11 mmol) was added at 0° C., then the mixture was naturally warmed up to 25° C. and stirred for 48 hours. The system was quenched by adding saturated ammonium chloride aqueous solution (10 mL). Ethyl acetate (15 mL*3) was added for extraction, then the phases were separated, and the organic phases were combined, dried by adding anhydrous sodium sulfate, filtered, and the filtrate was concentrated to dryness under reduced pressure to obtain compound 8-3. LCMS (ESI) m/z: 252[M+1]$^+$.

3) Synthesis of Compound 8-4

Compound 8-3 (543 mg, 2.16 mmol), anhydrous dichloromethane (6 mL) were added to a pre-dried single-necked flask, and the mixture was cooled down to 0° C., and thionyl chloride (1.2 g, 9.94 mmol, 721.24 µL) was added, then the mixture was stirred at 25° C. for 20 hours. Saturated brine (10 mL) was added to the system, the mixture was extracted with ethyl acetate (15 mL*3), and the organic phases were collected and combined, dried by adding anhydrous sodium sulfate, filtered, and the filtrate was concentrated to dryness under reduced pressure to obtain compound 8-4. LCMS (ESI) m/z: 270[M+1]$^+$.

4) Synthesis of Compound 8-6

Compound 8-4 (503 mg, 1.87 mmol), compound 1-5 (366 mg, 1.87 mmol), potassium carbonate (516 mg, 3.73 mmol), N,N-dimethylformamide (5 mL) were added to a pre-dried single-necked flask, and the mixture was stirred at 65° C. for 5 hours. The system was filtered, and the filter cake was rinsed with ethyl acetate (10 mL*3). The filtrate was collected and washed with saturated brine (10 mL*3), and the organic phase was concentrated to dryness under reduced pressure, then the crude product was purified by column chromatography to obtain compound 8-6. LCMS (ESI) m/z: 430[M+1]$^+$.

5) Synthesis of Compound 8-7

Compound 8-6 (450 mg, 1.05 mmol), anhydrous ethanol (5 mL), anhydrous tetrahydrofuran (5 mL), water (1.6 mL), sodium hydroxide (126 mg, 3.14 mmol) were added to a pre-dried single-necked flask, and the mixture was stirred at 65° C. for 17 hours. The pH of the system was adjusted to 3 by adding 0.5 M citric acid to the system, then the mixture was concentrated under reduced pressure, and the organic solvent in the system was evaporated to dryness by rotary evaporation, filtered, and the filter cake was rinsed with water (3 mL*3), collected, and dried under vacuum to obtain compound 8-7. LCMS (ESI) m/z: 402[M+1]$^+$.

6) Synthesis of Compound 8

Compound 8-7 (322 mg, 802.27 µmol), 1-8 (180 mg, 1.04 mmol), N,N-dimethylformamide (3 mL), N,N-diisopropylethylamine (467 mg, 3.61 mmol, 628.83 µL), HATU (458 mg, 1.20 mmol) were added to a pre-dried single-necked flask, and the mixture was stirred at 25° C. for 5 hours. The reaction mixture was purified by preparative high performance liquid chromatography (chromatographic column: Waters Xbridge Prep OBD C18 150*40 mm*10 µm; mobile phase: A-0.05 % ammonia water and 10 mM ammonium bicarbonate aqueous solution; B-acetonitrile; B %: 25 %-55 %, 8 min) to obtain compound 8. $^1$HNMR (400 MHz, DMSO-d$_6$) δ ppm 8.27 (t, J=5.2 Hz, 1 H), 7.96 (t, J=4.0 Hz, 1 H), 7.60 (m, 1 H), 7.19-7.07 (m, 3 H), 7.06-6.94 (m, 2 H), 6.43 (dd, J=5.6, 10.0 Hz, 1 H), 5.32 (s, 2 H), 5.05 (s, 2 H), 4.80 (dd, J=5.6, 8.4 Hz, 2 H), 4.67 (t, J=6.2 Hz, 2 H), 4.59-4.47 (m, 1 H), 4.38 (br d, J=5.0 Hz, 2 H), 3.81 (s, 3 H); LCMS (ESI) m/z: 557 [M+1]$^+$.

Embodiment 9

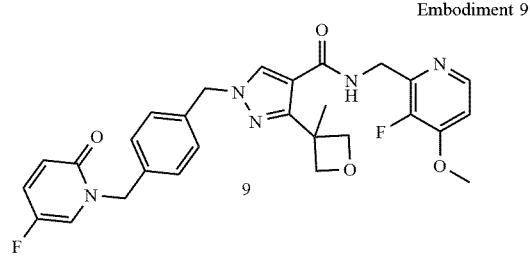

Synthetic route:

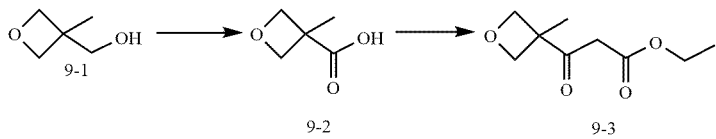

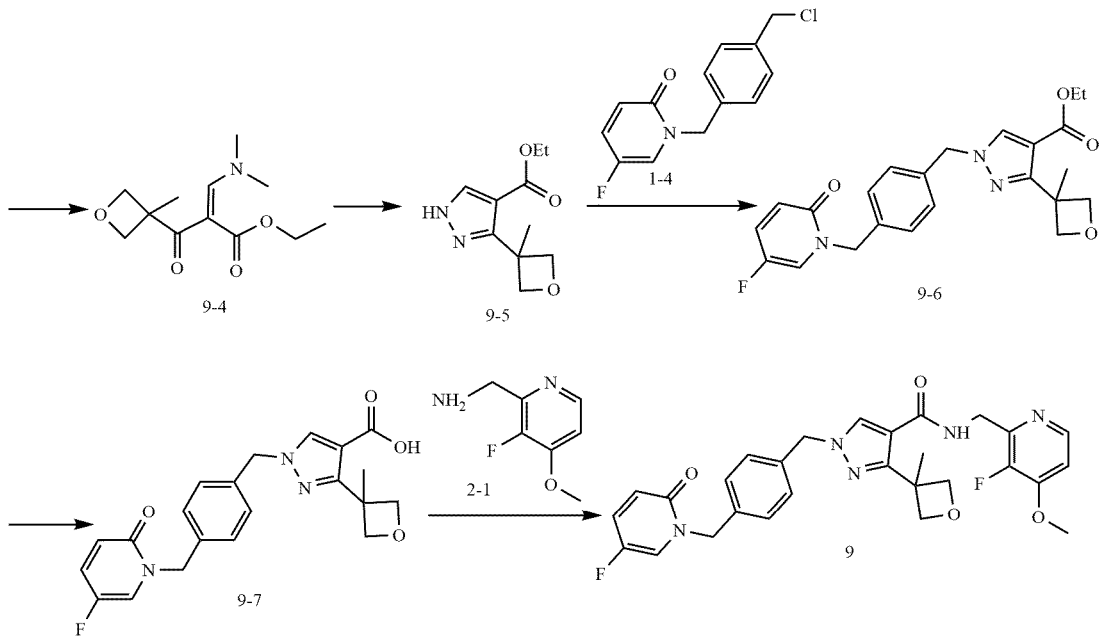

1) Synthesis of Compound 9-2

Compound 9-1(1 g, 9.79 mmol, 970.8 μL), diacetoxyiodobenzene (6.3 g, 19.58 mmol), water (10 mL), acetonitrile (10 mL) were added to a pre-dried reaction flask. The mixture was cooled down to 0° C. in an ice bath, and 2,2,6,6-tetramethylpiperidine oxide (307 mg, 1.96 mmol) was added thereto. Then the mixture was naturally warmed up to 20° C. and stirred for 12 hours. The reaction flask was quenched by adding sodium hydroxide solid (2.4 g) in an ice bath, stirred for 3 min, and methyl tert-butyl ether (20 mL) was added, then the mixture was extracted and the phases were separated twice, and the aqueous phase was collected. The aqueous phase was cooled down to 0° C. in an ice bath and the pH of the solution was adjusted to 3 by adding hydrochloric acid (12 M). Methyl tert-butyl ether (20 mL) was added, and the mixture was extracted and the phases were separated, and the organic phase was collected. Methyl tert-butyl ether (20 mL) was added to the aqueous phase, and the mixture was extracted and the phases were separated, and the organic phase was collected. The organic phases were combined, dried over anhydrous sodium sulfate, filtered, and the filtrate was concentrated under reduced pressure, then the crude product was purified by column chromatography to obtain compound 9-2. $^1$HNMR (400 MHz, CDCl$_3$) δ ppm 4.98 (d, J=5.70 Hz, 2 H), 4.42 (d, J=5.70 Hz, 2 H), 1.61 (s, 4 H); LCMS (ESI) m/z: 115 [M-1]$^-$.

2) Synthesis of Compound 9-3

Compound 9-2 (20 mg, 172.2 μmol), anhydrous tetrahydrofuran (1 mL) and N,N-carbonyldipyrazole (33 mg, 206.6 μmol) were added to a pre-dried reaction flask at 20° C. The mixture was stirred for 2 hours, then magnesium chloride (20 mg, 211.8 μmol, 8.6 μL) and ethyl potassium malonate (35 mg, 206.6 μmol) were added thereto and stirred for 4 hours. Ethyl acetate (5 mL) and water (5 mL) were added and the mixture was stirred for 5 minutes, then the mixture was extracted and the phases were separated, and the organic phase was collected. Ethyl acetate (10 mL*3) was added to the aqueous phase, and the organic phases were combined, and saturated brine (30 mL) was added to the organic phase, then the mixture was extracted and the phases were separated, and the organic phase was concentrated to dryness under reduced pressure to obtain compound 9-3. $^1$HNMR (400 MHz, CDCl$_3$) δ ppm 4.34-4.61 (m, 4 H), 3.34-3.77 (m, 2 H), 1.32-1.53 (m, 8 H); LCMS (ESI) m/z: 185 [M-1]$^-$.

3) Synthesis of Compound 9-4

Compound 9-3 (0.1 g, 537.1 μmol), N,N-dimethylformamide (2 mL), and 1,1-dimethoxytrimethylamine (128 mg, 1.07 mmol, 142.7 μL) were added to a pre-dried reaction flask, and the reaction was warmed up to 120° C. and carried out for 2 hours. The mixture was cooled down to 20° C. and concentrated under reduced pressure to obtain compound 9-4. LCMS (ESI) m/z: 242[M+1]$^+$.

4) Synthesis of Compound 9-5

Acetic acid (30 mg, 507.3 μmol, 29.1 μL) was added to a solution of compound 9-4 (120 mg, 497.3 μmol) and hydrazine hydrate (30 mg, 596.8 μmol, 29.6 μL) in n-butanol (1 mL), and the mixture was stirred at 110° C. for 2 hours. Ethyl acetate (5 mL) and saturated sodium bicarbonate aqueous solution (5 mL) were added and the mixture was stirred for minutes. The mixture was extracted and the phases were separated, and the aqueous phase was removed, then the organic phase was concentrated under reduced pressure to obtain compound 9-5. ¹HNMR (400 MHz, CDCl₃) δ ppm 8.04 (s, 1 H), 5.11 (d, J=6.14 Hz, 2 H), 4.69 (d, J=6.14 Hz, 2 H), 4.22-4.38 (m, 3 H), 1.76 (s, 4 H), 1.35-1.43 (m, 3 H); LCMS (ESI) m/z: 211 [M+1]⁺.

5) Synthesis of Compound 9-6

Compound 1-4 (118 mg, 470.9 µmol), compound 9-5 (0.1 g, 475.6 µmol), anhydrous potassium carbonate (138 mg, 1.00 mmol), N,N-dimethylformamide (2 mL) were added to a pre-dried thumb bottle at 25° C. The mixture was heated to 65° C. in an oil bath and stirred for 12 hours. The temperature was naturally cooled down to 20° C., then dichloromethane (10 mL) and water (10 mL) were added to the reaction flask, and the mixture was extracted and the phases were separated, and the organic phase was collected. Dichloromethane (10 mL) was added to the aqueous phase, and the organic phases were collected and combined. The organic phase was dried over anhydrous sodium sulfate, filtered and concentrated under reduced pressure to obtain compound 9-6. ¹HNMR (400 MHz, CDCl₃) δ ppm 8.02 (s, 1 H), 7.79 (s, 1 H), 7.10-7.41 (m, 6 H), 6.49-6.65 (m, 1 H), 5.17-5.28 (m, 1 H), 5.01-5.13 (m, 3 H), 4.64 (d, J=6.02 Hz, 1 H), 4.13-4.32 (m, 2 H), 1.73 (s, 3 H), 1.16-1.38 (m, 3 H); LCMS (ESI) m/z: 426 [M+1]⁺.

6) Synthesis of Compound 9-7

Compound 9-6 (0.3 g, 705.1 µmol) was added to a pre-dried reaction flask at 20° C. and dissolved in anhydrous tetrahydrofuran (2 mL), then sodium hydroxide solid (282 mg, 7.05 mmol), ethanol (2 mL) and water (2 mL) were added to the system. The mixture was warmed up to 60° C. and stirred for 12 hours. The reaction was naturally cooled down to 27° C., and hydrochloric acid (1 M, 10 mL) was added to the reaction flask to adjust the pH of the solution to 6, then dichloromethane (10 mL) and water (10 mL) were added to the reaction flask, and the mixture was extracted and the phases were separated, and the organic phase was collected. Dichloromethane (10 mL) was added to the aqueous phase, and the mixture was extracted and the phases were separated, then the organic phases were collected, combined, dried over anhydrous sodium sulfate, filtered, and concentrated under reduced pressure to obtain compound 9-7. LCMS (ESI) m/z: 398 [M+1]⁺.

7) Synthesis of Compound 9

Compound 9-7 (50 mg, 125.8 µmol), 2-1 (20 mg, 125.8 µmol), N,N-diisopropylethylamine (73 mg, 566.1 µmol, 98.6 µL), N,N-dimethylformamide (1.5 mL) were added to a pre-dried single-necked flask at 20° C., then the mixture was cooled down to 0° C., and HATU (71 mg, 188.7 µmol) was added thereto, and the mixture was stirred at 0° C. for 6 hours. The mixture was naturally warmed up to 20° C. and concentrated under reduced pressure to obtain the crude product. The crude product was purified by preparative high performance liquid chromatography (chromatographic column: Waters Xbridge BEH C18 100*25 mm*5 µm; mobile phase: A-10 mM ammonium bicarbonate aqueous solution; B-acetonitrile; B %: 15 %-50 %, 10 min) to obtain compound 9. ¹HNMR (400 MHz, DMSO-d₆) δ ppm 8.36-8.43 (m, 1 H), 8.24 (s, 1 H), 8.20 (d, J=5.29 Hz, 1 H), 8.02-8.08 (m, 1 H), 7.52-7.65 (m, 1 H), 7.29-7.33 (m, 2 H), 7.23-7.28 (m, 2 H), 7.14-7.19 (m, 1 H), 6.44 (dd, 7=10.14, 5.29 Hz, 1 H), 5.27 (s, 2 H), 5.02 (s, 2 H), 4.80 (d, J=6.17 Hz, 2 H), 4.45 (br d, J=3.75 Hz, 2 H), 4.40 (d, J=5.95 Hz, 2 H), 3.90 (s, 3 H), 1.54 (s, 3 H); LCMS (ESI) m/z: 536 [M+1]⁺.

Embodiment 10

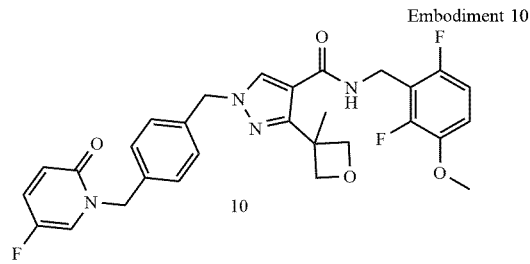

Synthetic route:

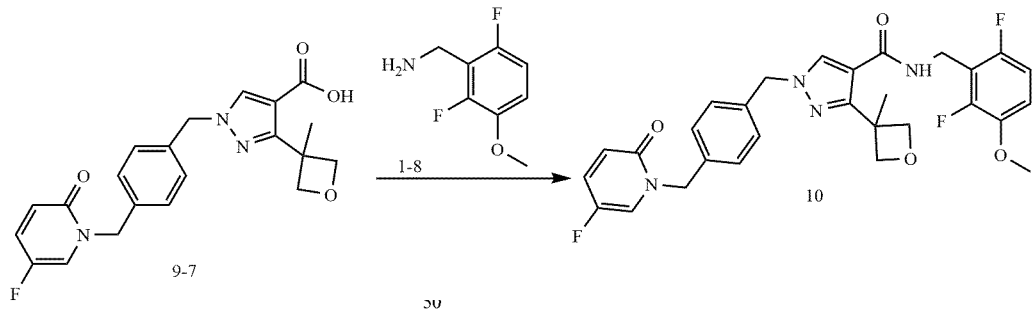

Synthesis of Compound 10

Compound 9-7 (49 mg, 125.5 µmol), 1-8 (26 mg, 150.6 µmol), N,N-diisopropylethylamine (72 mg, 564.7 µmol, 98.3 µL), N,N-dimethylformamide (1.5 mL) were added to a pre-dried single-necked flask at 20° C., then the mixture was cooled down to 0° C., and HATU (71 mg, 188.2 µmol) was added thereto, and the mixture was stirred for 2 hours. The reaction mixture was filtered, concentrated under reduced pressure to obtain the crude product, and the crude product was purified by preparative high performance liquid chromatography (chromatographic column: Waters Xbridge BEH C18 100*30 mm*10 µm; mobile phase: A-10 mM ammonium bicarbonate aqueous solution; B-acetonitrile; B %: 20 %-50 %, 8 min) to obtain compound 10. ¹HNMR (400 MHz, DMSO-d₆) δ ppm 8.82 (d, J=5.87 Hz, 1 H), 8.52 (d, J=6.36 Hz, 3 H), 8.32 (s, 1 H), 7.87-8.12 (m, 3 H), 7.47-7.73 (m, 1 H), 5.93 (s, 1 H), 5.63-5.83 (m, 3 H), 5.15-5.34 (m, 3 H), 4.57 (d, J=6.24 Hz, 2 H), 3.88 (s, J=6.24 Hz, 6 H), 1.97 (s, 1 H); LCMS (ESI) m/z: 553 [M+1]+.

Embodiment 11

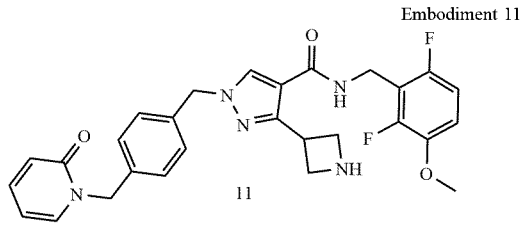

Synthetic route:

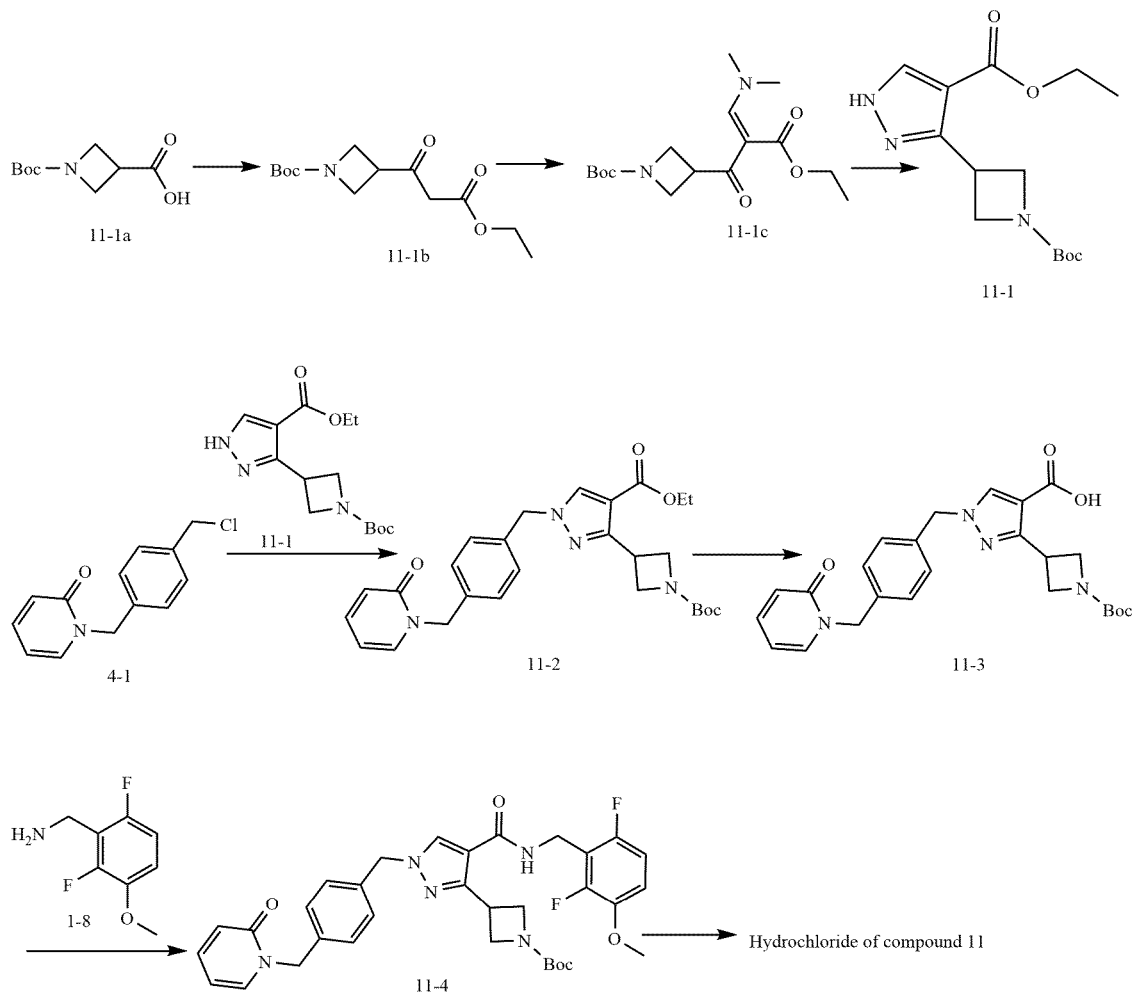

1) Synthesis of Compound 11-1b

Compound 11-1a (24.0 g, 119.27 mmol), 1,1-carbonyldiimidazole (23.2 g, 143.13 mmol), tetrahydrofuran (250 mL) were added to a pre-dried single-necked flask, then the mixture was purged with nitrogen for three times and stirred at 25° C. for 2 hours. Magnesium chloride (13.2 g, 146.71 mmol) and ethyl potassium malonate (24.3 g, 143.13 mmol) were added thereto, and the mixture was stirred at 25° C. for 4 hours. The system was evaporated to dryness by rotary evaporation, and ethyl acetate (300 mL) was added, then water (200 mL*4) was added for phase separation, and the organic phase was collected, dried over anhydrous sodium sulfate, filtered, and the filtrate was concentrated to dryness under reduced pressure and purified by column chromatography to obtain compound 11-1b. LCMS (ESI) m/z: 216 [M-55]+.

2) Synthesis of Compound 11-1c

Compound 11-1b (28.0 g, 103.20 mmol), N,N-dimethylformamide dimethyl acetal (24.6 g, 206.41 mmol, 27.42 mL), N,N-dimethylformamide (280 mL) were added to a pre-dried single-necked flask, and the mixture was stirred at 120° C. for 18 hours, then the system was cooled down to 60° C. and concentrated to dryness under reduced pressure to obtain the crude product of compound 11-1c. LCMS (ESI) m/z: 327 [M+1]+.

3) Synthesis of Compound 11-1

Compound 11-1c (32.0 g, 98.04 mmol), n-butanol (320 mL), glacial acetic acid (6.0 g, 100.00 mmol, 5.72 mL), hydrazine hydrate (5.7 g, 107.85 mmol, 5.52 mL) were added to a reaction flask, and the mixture was purged with nitrogen for three times, then the reaction was carried out at 110° C. for 7 hours. The reaction system was concentrated under reduced pressure and evaporated to dryness by rotary evaporation. The pH of the system was adjusted to 8 by adding saturated sodium bicarbonate aqueous solution, and the mixture was extracted by adding ethyl acetate (100 mL*3), then the organic phases were collected and combined, dried by adding anhydrous sodium sulfate, filtered, and the filtrate was concentrated to dryness under reduced pressure, and the crude product was purified by column chromatography to obtain compound 11-1. $^1$HNMR (400 MHz, CDCl$_3$) δ ppm 8.06 (s, 1 H), 4.38-4.12 (m, 7 H), 1.45 (s, 9 H), 1.35 (t, J=7.0 Hz, 3 H); LCMS (ESI) m/z: 240 [M-55]$^+$.

4) Synthesis of Compound 11-2

Compound 4-1 (330 mg, 1.41 mmol), compound 11-1 (500 mg, 1.69 mmol), N,N-dimethylformamide (5 mL), potassium carbonate (415 mg, 3.01 mmol) were added to a thumb bottle, and the mixture was purged with nitrogen for three times, then the reaction was carried out at 65° C. for 4 hours. Ethyl acetate (20 mL) and saturated brine (10 mL) were added to the reaction mixture, then the mixture was stirred for 5 minutes, and the phases were separated, and the organic phase was dried over anhydrous sodium sulfate, filtered, and concentrated under reduced pressure to obtain the crude product, and the crude product was purified by column chromatography to obtain compound 11-2. $^1$HNMR (400 MHz, DMSO-d$_6$) δ ppm 8.39 (s, 1 H), 7.75 (dd, J=6.78, 1.88 Hz, 1 H), 7.40 (ddd, J=8.97, 6.71, 2.01 Hz, 1 H), 7.25 (s, 4 H), 6.39 (d, J=9.03 Hz, 1 H), 6.19-6.25 (m, 1 H), 5.30 (s, 2 H), 5.06 (s, 2 H), 3.84-4.15 (m, 7 H), 1.36 (s, 9 H), 1.24 (t, J=7.09 Hz, 3 H).

5) Synthesis of Compound 11-3

Compound 11-2 (450 mg, 913.58 μmol), sodium hydroxide (109 mg, 2.74 mmol), ethanol (6 mL), water (2 mL) were added to a thumb bottle, and the mixture was purged with nitrogen for three times, then the reaction was carried out at 25° C. for 16 hours, then additional sodium hydroxide (36 mg, 913.58 μmol) was added and the reaction was continued at 25° C. for 4 hours. Citric acid aqueous solution (0.5 M) was added dropwise to the reaction mixture to adjust the pH to 4-5, then ethyl acetate (20 mL) was added to the reaction mixture, and the organic phase was dried over anhydrous sodium sulfate, filtered, and concentrated under reduced pressure to obtain the crude product, then the crude product was purified by column chromatography to obtain compound 11-3. $^1$HNMR (400 MHz, MeOD) δ ppm 8.11 (s, 1 H), 7.69 (d, J=4.52 Hz, 1 H), 7.48-7.58 (m, 1 H), 7.24-7.35 (m, 4 H), 6.57 (d, J=9.03 Hz, 1 H), 6.39 (t, J=6.27 Hz, 1 H), 5.31 (s, 2 H), 5.19 (s, 2 H), 4.06-4.29 (m, 5 H), 1.44 (s, 9 H).

6) Synthesis of Compound 11-4

Compound 11-3 (200 mg, 430.56 μmol), compound 1-8 (74 mg, 430.56 μmol), N,N-dimethylformamide (2 mL), diisopropylethylamine (250 mg, 1.94 mmol) were added to a three-necked flask, then the mixture was cooled down to 0° C., and HATU (245 mg, 645.84 μmol) was added thereto, and the mixture was naturally warmed up to 25° C. and stirred for 1 hour. Ethyl acetate (20 mL) and saturated brine (10 mL) were added to the reaction mixture, and the mixture was stirred for 5 minutes, and the phases were separated, then the organic phase was dried over anhydrous sodium sulfate, filtered, and concentrated under reduced pressure to obtain the crude product, then the crude product was purified by thin-layer chromatography on silica gel plate to obtain compound 11-4. LCMS (ESI) m/z: 620[M+1]$^+$.

7) Synthesis of Hydrochloride of Compound 11

Compound 11-4 (50 mg, 80.69 μmol), hydrochloric acid/ethyl acetate (6 M, 12.49 mL) were added to a reaction flask, and the mixture was purged with nitrogen for three times, then the reaction was carried out at 25° C. for 1 hour. The reaction mixture was concentrated under reduced pressure to obtain the crude product, and the crude product was purified by preparative high performance liquid chromatography (chromatographic column: Phenomenex Luna C18 100*30 mm*5 μm; mobile phase: A-0.04 % hydrochloric acid aqueous solution; B-acetonitrile; B %: 10 %-40 %, 10 min) to obtain hydrochloride of compound 11. $^1$HNMR (400 MHz, DMSO-d$_6$) δ ppm 8.98 (brs, 1 H), 8.53-8.72 (m, 1 H), 8.42 (t, J=5.08 Hz, 1 H), 8.29 (s, 1 H), 7.78 (dd, J=6.78, 1.88 Hz, 1 H), 7.41 (ddd, J=9.00, 6.68, 2.01 Hz, 1 H), 7.20-7.33 (m, 4 H), 7.12 (td, J=9.32, 5.21 Hz, 1 H), 6.96-7.05 (m, 1 H), 6.39 (d, J=9.16 Hz, 1 H), 6.23 (td, J=6.65, 1.13 Hz, 1 H), 5.29 (s, 2 H), 5.06 (s, 2 H), 4.28-4.44 (m, 3 H), 4.04-4.21 (m, 4 H), 3.81 (s, 3 H); LCMS (ESI) m/z: 520 [M+1]$^+$.

Embodiment 12

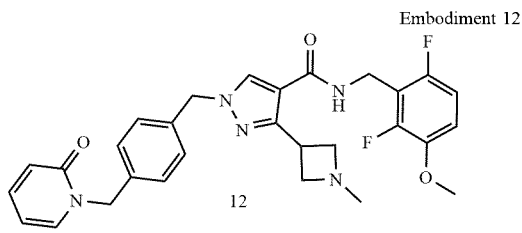

Synthetic route:

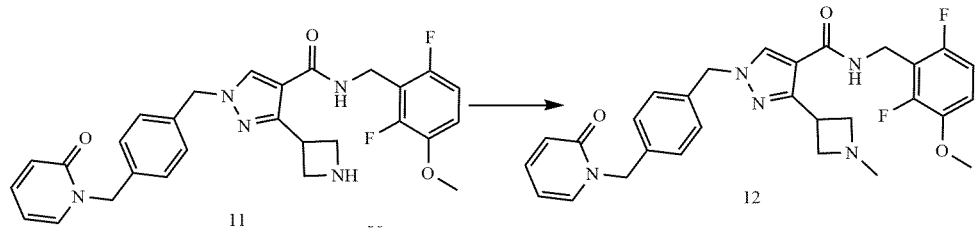

1) Synthesis of Compound 12

Compound 11 (15 mg, 28.87 μmol), methanol (1 mL), paraformaldehyde (26 mg, 288.72 μmol) were added to a reaction flask, and the mixture was stirred for 0.5 hours, then sodium cyanoborohydride (9 mg, 144.36 μmol) was added thereto, and the mixture was stirred at 25° C. for 0.5 hours. The dilute hydrochloric acid aqueous solution (1 M, 1 mL) was added to the reaction mixture, and the mixture was stirred for 1 min, then filtered, and the filtrate was collected. The filtrate was concentrated under reduced pressure to obtain the crude product, and the crude product was purified by preparative high performance liquid chromatography (chromatographic column: Phenomenex Luna C18 100*30 mm*5 μm; mobile phase: A-0.04 % hydrochloric acid aqueous solution; B-acetonitrile; B %: 15 %-45 %, 10 min) to obtain hydrochloride of compound 12. ¹HNMR (400 MHz, D₂O) δ ppm 7.98-8.08 (m, 1 H), 7.56 (br d, J=7.15 Hz, 2 H), 7.10 (br s, 4 H), 6.97 (br d, J=5.90 Hz, 1 H), 6.78-6.88 (m, 1 H), 6.54 (br d, J=8.41 Hz, 1 H), 6.43 (br d, J=5.40 Hz, 1 H), 5.22 (br s, 2 H), 5.06 (br s, 2 H), 4.98-5.12 (m, 1 H), 4.37-4.54 (m, 4 H), 3.98-4.35 (m, 3 H), 3.75 (br s, 3 H), 2.90 (s, 1 H), 2.77 (s, 2 H); LCMS (ESI) m/z: 534 [M+1]⁺.

100*30 mm*5 μm; mobile phase: A-0.04 % hydrochloric acid aqueous solution; B-acetonitrile; B %: 20 %-50 %, 10 min) to obtain compound 13. ¹HNMR (400 MHz, DMSO-d₆) δ ppm 8.29 (br t, J=5.02 Hz, 1 H), 8.21 (s, 1 H), 7.76 (dd, J=6.71, 1.69 Hz, 1 H), 7.41 (ddd, J=8.94, 6.74, 1.88 Hz, 1 H), 7.24 (q, J=8.24 Hz, 4 H), 7.07-7.16 (m, 1 H), 6.96-7.05 (m, 1 H), 6.39 (d, J=9.03 Hz, 1 H), 6.22 (t, J=6.65 Hz, 1 H), 5.27 (s, 2 H), 5.06 (s, 2 H), 4.32-4.44 (m, 3 H), 4.03-4.18 (m, 3 H), 3.94 (br d, J=3.76 Hz, 1 H), 3.81 (s, 3 H), 1.73 (s, 3 H); LCMS (ESI) m/z: 562 [M+1]⁺.

Embodiment 14

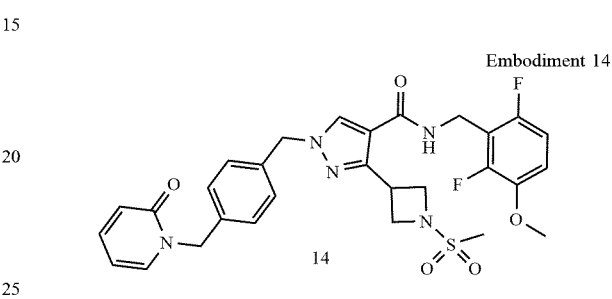

Embodiment 13

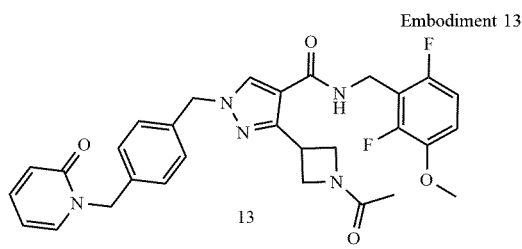

Synthetic route:

Synthetic route:

1) Synthesis of Compound 13

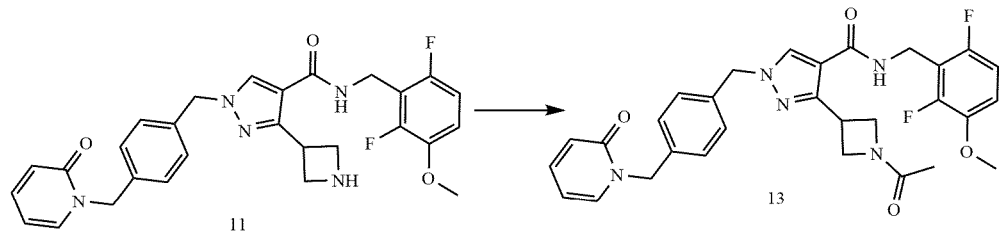

Synthesis of Compound 14

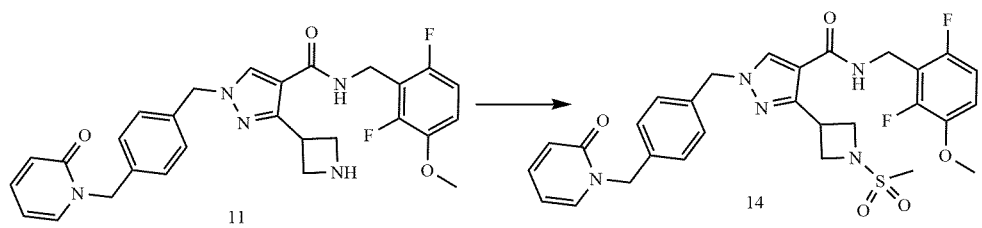

Compound 11 (10 mg, 19.25 μmol), N,N-dimethylformamide (1 mL), triethylamine (2 mg, 19.25 μmol) were added to a reaction flask, and the temperature was cooled down to 0° C., then acetic anhydride (2 mg, 19.25 μmol) was added thereto, and the reaction was naturally warmed up to 25° C. and carried out for 2 hours. The reaction mixture was concentrated under reduced pressure to obtain the crude product, and the crude product was purified by preparative high performance liquid chromatography (chromatographic column: Phenomenex Luna C18

Compound 11 (70 mg, 134.73 μmol), dichloromethane (1 mL), triethylamine (41 mg, 404.20 μmol) were added to a reaction flask, and the temperature was cooled down to 0° C., then methylsulfonyl chloride (38 mg, 336.84 μmol) was added thereto, and the mixture was stirred at 0° C. for 3 hours. The reaction mixture was added with saturated sodium bicarbonate aqueous solution (2 mL), extracted with dichloromethane (5 mL*3), and the phases were separated, and the organic phases were combined, washed with saturated brine (2 mL*3), dried over anhydrous sodium sulfate, filtered and concentrated under reduced pressure to obtain the crude product, and the crude product was purified by preparative high performance liquid chromatography (chromatographic column: Phenomenex Gemini-NX C18 75*30 mm*3 μm; mobile phase: A- 10 mM ammonium bicarbonate aqueous solution; B- methanol; B %: 45 %-75 %, 10.5 min) to obtain compound 14. $^1$HNMR (400 MHz, DMSO-$d_6$) δ ppm 8.33 (t, J=5.08 Hz, 1 H), 8.22 (s, 1 H), 7.76 (dd, J=6.71, 1.95 Hz, 1 H), 7.41 (ddd, J=9.00, 6.68, 2.01 Hz, 1 H), 7.20-7.30 (m, 4 H), 7.11 (td, J=9.32, 5.33 Hz, 1 H), 6.96-7.04 (m, 1 H), 6.39 (d, J=9.16 Hz, 1 H), 6.22 (td, J=6.65, 1.25 Hz, 1 H), 5.28 (s, 2 H), 5.06 (s, 2 H), 4.38 (br d, J=4.89 Hz, 2 H), 4.09-4.15 (m, 3 H), 3.95-4.01 (m, 2 H), 3.81 (s, 3 H), 2.92 (s, 3 H); LCMS (ESI) m/z: 598 [M+1]$^+$.

Embodiment 15

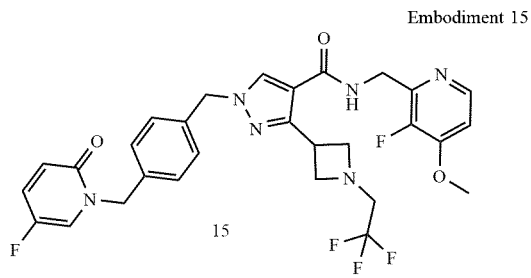

Synthetic route:

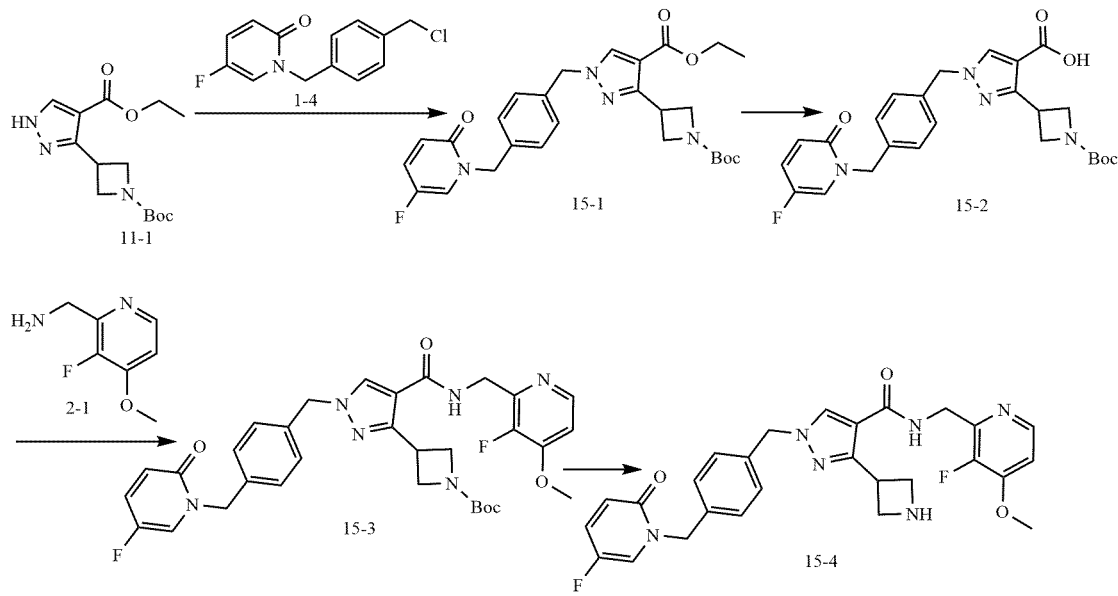

1) Synthesis of Compound 15-1

Compound 11-1 (1.3 g, 5.17 mmol), compound 1-4 (1.7 g, 5.68 mmol), potassium carbonate (1.5 g, 11.00 mmol), N,N-dimethylformamide (10 mL) were added to a pre-dried single-necked flask, and the mixture was stirred at 65° C. for 3 hours. The system was filtered, and the filter cake was rinsed with ethyl acetate (10 mL*3), and the filtrate was collected and washed with saturated brine (10 mL*3), then the organic phase was collected, dried over anhydrous sodium sulfate, filtered, and the filtrate was concentrated under reduced pressure to obtain the crude product, and the the crude product was purified by column chromatography to obtain compound 15-1. LCMS (ESI) m/z: 511 [M+1]$^+$.

2) Synthesis of Compound 15-2

Compound 15-1 (1.0 g, 1.96 mmol), sodium hydroxide (235 mg, 5.88 mmol), ethanol (5 mL), tetrahydrofuran (5 mL), water (1.6 mL) were added to a pre-dried single-necked flask, and the mixture was stirred at 75° C. for 16 hours. The system was added with saturated citric acid aqueous solution to adjust the pH to 3, then the mixture was extracted with ethyl acetate (10 mL*3), and the organic phases were collected and combined, washed by adding saturated brine (20 mL), dried over anhydrous sodium sulfate, filtered, and the filtrate was concentrated under reduced pressure to obtain compound 15-2. LCMS (ESI) m/z: 383 [M-99]$^+$.

3) Synthesis of Compound 15-3

Compound 15-2 (797 mg, 1.65 mmol), compound 2-1 (258 mg, 1.65 mmol), N,N-dimethylformamide (0.9 mL), N,N-diisopropylethylamine (961 mg, 7.43 mmol, 1.29 mL), HATU (942 mg, 2.48 mmol) were added to a pre-dried three-necked flask, then the mixture was stirred at 0° C. for 2 hours. The system was added with saturated brine (20 mL), extracted with ethyl acetate (15 mL*3), and the organic phases were collected, dried over anhydrous sodium sulfate, filtered, and the filtrate was concentrated under reduced pressure to obtain the crude product, and the crude product was purified by column chromatography to obtain compound 15-3. LCMS (ESI) m/z: 621[M+1]⁺.

4) Synthesis of Compound 15-4

Compound 15-3 (503 mg, 810.45 μmol), ethyl acetate (1 mL), hydrochloric acid/ethyl acetate (4 M, 5 mL) were added to a pre-dried single-necked flask, and the mixture was stirred at 23° C. for 1 hour. The solvent in the system was concentrated under reduced pressure to obtain compound 15-4.

5) Synthesis of Compound 15

Compound 15-4 (169 mg, 303.42 μmol), trifluoroethyl trifluoromethanesulfonate (176 mg, 758.54 μmol), N,N-diisopropylethylamine (137 mg, 1.06 mmol, 184.97 μL), tetrahydrofuran (0.8 mL), N,N-dimethylformamide (0.8 mL) were added to a pre-dried single-necked flask, and the mixture was stirred at 27° C. for 4 hours. The reaction mixture was concentrated under reduced pressure to obtain the crude product, and the crude product was purified by thin layer chromatography (dichloromethane/methanol=20/1) to obtain compound 15. ¹HNMR (400 MHz, DMSO-d₆) δ ppm 8.34 (s, 1 H), 8.24-8.17 (m, 2 H), 8.04 (br d, J=3.8 Hz, 1 H), 7.63-7.54 (m, 1 H), 7.35-7.22 (m, 4 H), 7.17 (t, J=5.8 Hz, 1 H), 6.45 (dd, J=5.6, 10.2 Hz, 1 H), 5.28 (s, 2 H), 5.03 (s, 2 H), 4.47 (br d, J=3.4 Hz, 2 H), 4.07-3.95 (m, 1 H), 3.92 (s, 3 H), 3.68 (br t, J=7.2 Hz, 2 H), 3.41 (br t, J=7.4 Hz, 3 H), 3.16 (q, J=9.8 Hz, 2 H); LCMS (ESI) m/z: 603 [M+1]⁺.

Synthesis of Compound 16

Under nitrogen protection, N,N-diisopropylethylamine (1.41 g, 10.95 mmol) and HATU (3.12 g, 8.21 mmol) were added to a solution of compound 4-3 (2.0 g, 5.47 mmol) in N,N-dimethylformamide (20 mL) in an ice-water bath at 0° C., and the mixture was stirred for 30 min, then compound 1-8 (1 g, 5.78 mmol) was added thereto, and the resulting mixture was naturally warmed up to room temperature of 25° C. and stirred for 16 hours. The reaction mixture was added with ethyl acetate (100 mL) and water (50 mL), stirred for 10 minutes, and the organic phase was collected, dried over anhydrous sodium sulfate, filtered, and concentrated under reduced pressure to obtain the crude product, and the crude product was purified by column chromatography (gradient elution: methanol/dichloromethane, methanol %: 0 to 10 %, flow rate of 60 mL/min) to obtain compound 16. ¹HNMR (400 MHz, CD₃OD) δ ppm 8.02 (s, 1 H), 7.69 (dd, J=6.7, 1.8 Hz, 1 H), 7.52 (ddd, J=9.0, 6.8, 2.0 Hz, 1 H), 7.29 (q, J=8.4 Hz, 4 H), 7.03 (br d, J=5.1 Hz, 1 H), 6.88 (br d, J=2.0 Hz, 1 H), 6.57 (d, J=9.0 Hz, 1 H), 6.35-6.41 (m, 1 H), 5.29 (s, 2 H), 5.18 (s, 2 H), 4.98 (dd, J=8.5, 5.8 Hz, 2 H), 4.90 (br s, 2 H), 4.65 (s, 1 H), 4.51 (s, 2 H), 3.84 ppm (s, 3 H); LCMS (ESI) m/z: 521 [M+1]⁺.

Embodiment 17

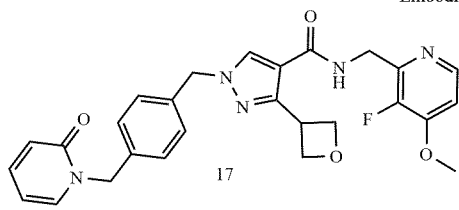

Embodiment 16

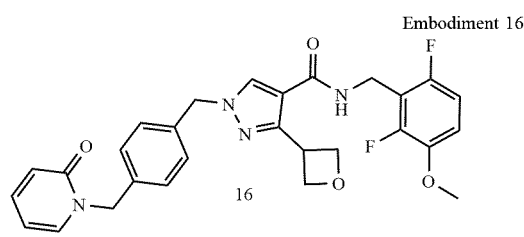

Synthetic route:

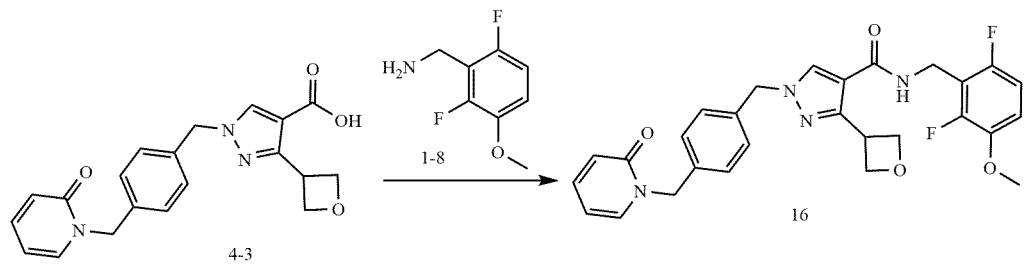

Synthetic route:

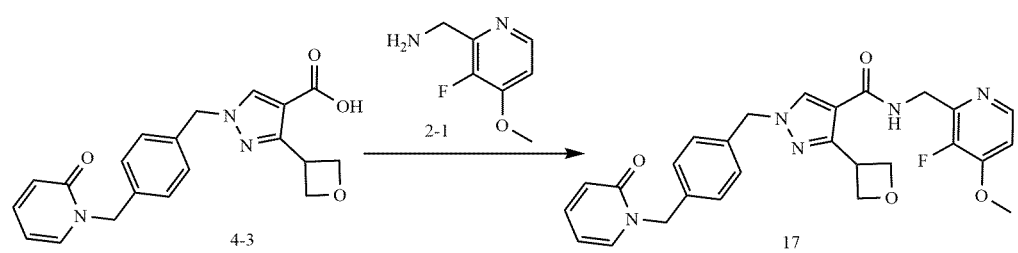

Synthesis of Compound 17

Under nitrogen protection, N,N-diisopropylethylamine (106.2 mg, 821.6 µmol) and HATU (124.9 mg, 328.4 µmol) were added to a solution of compound 4-3 (100 mg, 273.7 µmol) and compound 2-1 (63.2 mg, 328.4 µmol) in N,N-dimethylformamide (1 mL) at room temperature of 25° C., and the resulting mixture was stirred for 16 hours. The reaction mixture was added with ethyl acetate (5 mL) and water (3 mL), and stirred for 5 minutes, then the aqueous phase was removed, and the organic phase was concentrated under reduced pressure, and the crude product was purified by preparative high performance liquid chromatography (chromatographic column: Welch Xtimate C18 150*25 mm*5 µm; mobile phase: A-10 mM ammonium bicarbonate aqueous solution; B-acetonitrile; B %: 25 %-55 %, 10.5 min) to obtain compound 17. $^1$HNMR (400 MHz, CD$_3$OD) δ ppm 8.17 (d, J=5.6, 1 H), 8.10 (s, 1 H), 7.70 (m, 1 H), 7.52 (m, 1 H), 7.28-7.34 (m, 4 H), 7.11-7.14 (m, 1 H), 6.56-6.58 (m, 1 H), 6.38-6.40 (m, 1 H), 5.32 (s, 1 H), 5.19 (s, 1 H), 4.97-4.99 (m, 4 H), 4.62-4.66 (m, 2 H), 4.57 (s, 2 H), 3.96 (s, 3 H); LCMS (ESI) m/z: 504 [M+1]$^+$.

Embodiment 18

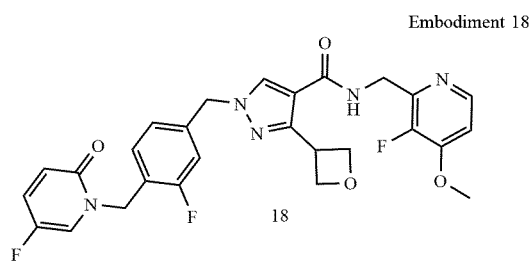

Synthetic route:

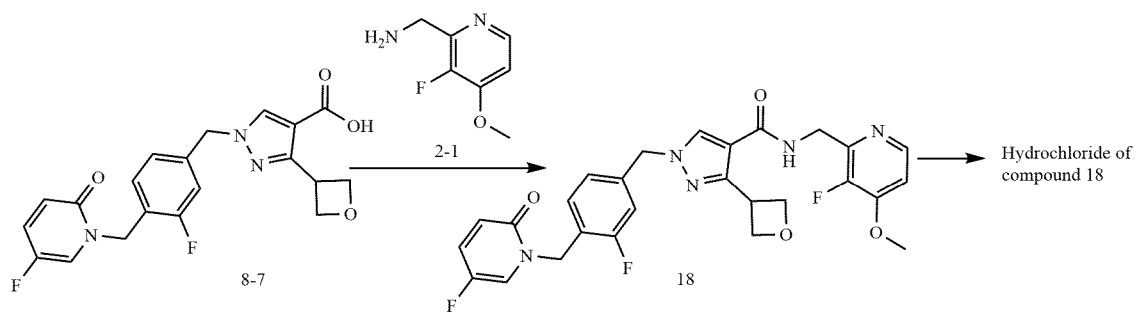

1) Synthesis of Compound 18

Compound 8-7 (200 mg, 498.30 µmol), tetrahydrofuran (3 mL) were added to a pre-dried single-necked flask, then N,N-diisopropylethylamine (225.41 mg, 1.74 mmol, 303.78 µL), N,N'-carbonyl diimidazole (105.04 mg, 647.79 mmol) were added thereto, and the mixture was stirred at 50° C. for 1 hour, then compound 2-1 (115.18 mg, 597.96 µmol) was added thereto. The mixture was stirred at 50° C. for 16 hours, and additional 2-1 (23.34 mg, 121.09 µmol) was added, then the mixture was stirred at 50° C. for 3 hours, and then additional compound 2-1 (22 mg, 114.22 µmol) was added, and the reaction was stirred at 50° C. for 16 hours. The reaction mixture was concentrated under reduced pressure, dissolved by adding N,N-dimethylformamide (3 mL), filtered, and the filtrate was concentrated under reduced pressure and purified by preparative high performance liquid chromatography (chromatographic column: Waters Xbridge BEH C18 100*30 mm*10 µm; mobile phase: A-10 mM ammonium bicarbonate aqueous solution; B-acetonitrile; B %: 15 %-45 %, 8 min) to obtain target compound 18. $^1$HNMR (400 MHz, DMSO-d$_6$) δ ppm 8.39 (t, J=5.7 Hz, 1 H), 8.29 (s, 1 H), 8.21 (d, J=5.7 Hz, 1 H), 7.98-7.93 (m, 1 H), 7.60 (ddd, J=3.5, 7.0, 10.1 Hz, 1 H), 7.19-7.12 (m, 3 H), 7.09-7.05 (m, 1 H), 6.44 (dd, J=5.7, 10.1 Hz, 1 H), 6.10-6.08 (m, 1 H), 5.34 (s, 2 H), 5.06 (s, 2 H), 4.81-4.76 (m, 2 H), 4.67 (dd, J=5.7, 7.0 Hz, 2 H), 4.56-4.43 (m, 3 H), 3.91 (s, 3 H).

2) Synthesis of Hydrochloride of Compound 18

Compound 18 (42.8 mg, 79.33 µmol), acetonitrile (20 mL) were added to a pre-dried single-necked flask, and the mixture was sonicated and dissolved to clear, then dilute hydrochloric acid (1.1 M, 72.12 µL) was added thereto, and the reaction was stirred at 15° C. for 3 hours, then the reaction mixture was filtered under reduced pressure and the filter cake was rinsed with acetonitrile (5 mL), filtered to dryness and continued to filter under reduced pressure for 2 hours to remove the residual acetonitrile, and the filter cake was collected and dried to obtain hydrochloride of compound 18. $^1$HNMR (400 MHz, DMSO-d$_6$) δ ppm 8.46 (s, 1 H), 8.34-8.23 (m, 2 H), 7.97 (t, J=3.9 Hz, 1 H), 7.61 (s, 1 H), 7.25 (s, 1 H), 7.19-7.11 (m, 2 H), 7.09-7.04 (m, 1 H), 6.44 (dd, J=5.3, 10.1 Hz, 1 H), 5.35 (s, 2 H), 5.06 (s, 2 H), 4.78 (dd, J=5.7, 8.3 Hz, 2 H), 4.71-4.64 (m, 2 H), 4.53-4.44 (m, 3 H), 3.95 (s, 3H); LCMS (ESI) m/z: 540 [M+1]$^+$.

Experimental Embodiment 1: Inhibitory Effect of Test Compounds on Plasma Kallikrein (PKAL)

1. PKal reaction buffer: 25 mM Tris-HCl (trometamol-HCl), pH 8.0, 100 mM NaCl, pH 8.5, 0.01 % Brij35 (polyoxyethylene lauryl ether), and 1 % DMSO (final concentration).

2. Enzyme: PKal (R&D Systems Cat# 2497-SE), recombinant human plasma kallikrein expressed in a mouse myeloma cell line, Gly20-Ala638 derived from NS0- with a 60-His appendage at the C-terminus, MW=70 kDa. Activation of the enzyme: (1) rhPKal was diluted to 200 µg/mL activation buffer (100 mM Tris, 10 mM CaCl$_2$, 150 mM NaCl, pH 7.5 (TCN)); (2) thermolysin was diluted to 20 µg/mL activation buffer; (3) rhPKal (200 µg/mL) and thermolysin (20 µg/mL) were mixed in equal volumes; (4) the mixture was incubated at 37° C. for 30 min; (5) then the reactions was stopped with 50 µM EDTA (ethylenediaminetetraacetic acid).

3. Substrate (Enzo Cat# P-139): 10 µM Z-FR-AMC (AMC: 7-amino-4-methylcoumarin).

4. Detection: EnVision (PE), Ex/Em 355/460 nm.

5. Reaction process: (1) The specified enzymes and substrates were prepared in freshly prepared activation buffer; (2) the enzyme solution was injected into the reaction hole; (3) the DMSO solution of the test compound was injected into the reaction mixture, and controlled within the nanoliter range using acoustic technology (Echo 550, LabCyte Inc. Sunnyvale, CA); (4) after 10 min of pre-incubation, the substrate solution was injected into the reaction hole to start the reaction; (5) the activity of the enzyme could be indicated by the increase of the fluorescence signal of the fluorescent labeled peptide substrate, which was monitored every 5 min and lasted for 120 min at room temperature; (6) data analysis: the slope* (fluorescence signal/time) of the straight line was measured, then the slope could be calculated by excel and the curve could be fitted by Prism software. The test results of the inhibitory effect of the compounds on plasma kallikrein (Pkal) are shown in Table 1 below.

TABLE 1

Test results of the inhibitory effect of the compounds on plasma kallikrein

| Number of the compound | $IC_{50}$ (Human PKal) nM | Number of the compound | $IC_{50}$ (Human PKal) nM |
|---|---|---|---|
| Compound 1 | 0.139 | Compound 10 | 0.344 |
| Compound 2 | 1.53 | Hydrochloride of compound 11 | 0.269 |
| Compound 3 | 0.264 | Hydrochloride of compound 12 | 1.08 |
| Compound 4 | 0.052 | Compound 13 | 0.833 |
| Compound 5 | 18.7 | Compound 14 | 0.717 |
| Compound 6 | 2.63 | Compound 15 | 2.24 |
| Compound 7 | 0.552 | Compound 16 | 0.62 |
| Compound 8 | 0.465 | Compound 17 | 0.053 |
| Compound 9 | 1.03 | Hydrochloride of compound 18 | 2.31 |

Experimental conclusion: The compounds of the present disclosure display significant inhibitory effect on plasma kallikrein (PKal).

Experimental Embodiment 2: Pharmacokinetic Test of the Compounds of The Present Disclosure 1. Abstract Male SD rats were used as test animals, and LC-MS/MS method was used to determine the drug concentrations in plasma of rats at different times after intravenous and intragastric administration of test compounds. The pharmacokinetic behaviors of the compounds in rats were studied and the pharmacokinetic characteristics were evaluated.

2. Experimental Protocol 2.1 Test drug: Test compound.

2.2 Test animals: 28 healthy adult male SD rats were divided into 14 groups with 2 rats in each group. Animals were purchased from Beijing Vital River Laboratory Animal Technology Co., Ltd.

2.3 Drug Preparation

An appropriate amount of sample was weighed, and an appropriate amount of DMSO, polyoxyethylene castor oil and sterile water for injection were added in sequence according to the volume ratio of 10:10:80, then the mixture was stirred and sonicated to reach a clear state of 0.5 mg/mL for intravenous administration.

An appropriate amount of sample was weighed, and an appropriate amount of DMSO, polyoxyethylene castor oil and sterile water for injection were added in sequence according to the volume ratio of 10:10:80, then the mixture was stirred and sonicated to reach a clear or suspension state of 0.4 mg/mL for intragastric administration.

An appropriate amount of sample was weighed, and an appropriate amount of DMSO, polyoxyethylene castor oil and sterile water for injection were added in sequence according to the volume ratio of 10:10:80, then the mixture was stirred and sonicated to reach a clear state of 3 mg/mL for intravenous administration.

2.4 Administration: 28 male SD rats were divided into 14 groups, after fasting for one night, the intravenous administration group was administered with an administration volume of 2 mL/kg and a dose of 1 mg/kg; the intragastric administration group 1 was administered with an administration volume of 5 mL/kg and a dose of 2 mg/kg. The intragastric administration group 2 was administered with an administration volume of 10 mL/kg and a dose of 30 mg/kg.

3. Experimental Operations and Results

After the compound was administered intravenously to male SD rats, 40 μL of blood was collected at 0.0833, 0.25, 0.5, 1, 2, 4, 8 and 24 hours, respectively, and placed in tubes containing 2 μL of EDTA-$K_2$. After the compound was administered in the intragastric administration group, 40 μL of blood was collected at 0.25, 0.5, 1, 2, 4, 6, 10 and 24 hours, respectively, and placed in tubes containing 2 μL of EDTA-$K_2$. The tubes were centrifuged at 4000 rpm for 15 minutes to separate the plasma, and stored at -60° C. Animals were allowed to eat 2 hours after administration.

LC-MS/MS method was used to determine the content of the test compounds in the plasma of rats after intravenous and intragastric administration. The linear range of the method was 2.00 - 6000 nmol/L; plasma samples were treated with acetonitrile to precipitate protein, and then analyzed. The pharmacokinetic test results of the compounds are shown in Table 2 below.

TABLE 2

Pharmacokinetic test results of the compounds

| Test compound | Administration method | Administration dose mg/kg | Plasma drug concentration $C_{max}$ (nM) | Peak time $T_{max}$ (h) | Half-life $T_{½}$ (h) | Apparent volume of distribution Vdss (L/kg) | Clearance rate Cl (mL/min/kg) | Curve area (o-t) $AUC_{0-last}$ (nM·h) | Curve area (o-inf) $AUC_{0-inf}$ (nM·h) | Bioavailability F (%) |
|---|---|---|---|---|---|---|---|---|---|---|
| Compound 1 | intravenous administration | 0.918 | - | - | 0.624 | 0.202 | 7.09 | 4352 | 4375 | - |
| | intragastric administration 1 | 1.71 | 1135 | 0.5 | 1.56 | - | - | 1331 | 1337 | 15.3 |

TABLE 2-continued

Pharmacokinetic test results of the compounds

| Test compound | Administration method | Administration dose mg/kg | Plasma drug concentration $C_{max}$ (nM) | Peak time $T_{max}$ (h) | Half-life $T_{1/2}$ (h) | Apparent volume of distribution Vdss (L/kg) | Clearance rate Cl (mL/min/kg) | Curve area (o-t) $AUC_{0\text{-}last}$ (nM·h) | Curve area (o-inf) $AUC_{0\text{-}inf}$ (nM·h) | Bioavailability F (%) |
|---|---|---|---|---|---|---|---|---|---|---|
| Compound 2 | intragastric administration | 2.00 | 301 | 0.25 | 0.436 | - | - | 241 | 246 | - |
| Compound 3 | intravenous administration | 1.34 | - | - | 0.713 | 0.169 | 7.85 | 5491 | 5497 | - |
|  | intragastric administration 1 | 2.1 | 1755 | 0.5 | 1.37 | - | - | 2107 | 2125 | 19.3 |
| Compound 4 | intravenous administration | 1.07 | - | - | 0.605 | 0.182 | 8.26 | 3935 | 3947 | - |
|  | intragastric administration 1 | 2.38 | 1548 | 0.375 | 1.28 | - | - | 1791 | 1800 | 22.7 |
| Compound 6 | intragastric administration | 2.18 | 650 | 0.375 | 2.34 | - | - | 653 | 661 | - |
| Compound 7 | intragastric administration | 24.7 | 813 | 0.5 | 2.61 | - | - | 1845 | 1933 | - |
| Compound 8 | intravenous administration | 1.04 | - | - | 0.392 | 0.188 | 12.2 | 2617 | 2621 | - |
|  | intragastric administration 1 | 2.08 | 680 | 0.25 | 1.57 | - | - | 584 | 591 | 11.2 |
|  | intragastric administration 2 | 26.1 | 18600 | 0.25 | 1.92 | - | - | 42405 | 42469 | 54 |
| Compound 16 | intravenous administration | 1.03 | - | - | 0.596 | 0.2 | 7.3 | 4369 | 4389 | - |
|  | intragastric administration | 2.02 | 1135 | 0.75 | 2.27 | - | - | 1930 | 1940 | 22.1 |
| Compound 17 | intragastric administration | 2.00 | 230 | 0.5 | 0.846 | - | - | 237 | 246 | - |

Note: "-" means that the item is not detected.

Experimental conclusion: The compounds of the present disclosure have a low clearance rate, a certain oral exposure and oral bioavailability.

Experimental Embodiment 3: Pharmacokinetic Test of the Compounds of The Present Disclosure in Rat Eyes 1. Abstract Male SD rats were used as test animals, and LC-MS/MS method was used to determine the drug concentrations in eye tissues at different times after intragastric administration of the test compound. The pharmacokinetic behavior of the compounds in the eyes of rats after intragastric administration was studied, and the pharmacokinetic characteristics were evaluated.

2. Experimental Protocol 2.1 Test drug: Test compound
2.2 Test animals: Six healthy adult male rats were divided into three groups with 4 eyes in each group. Animals were purchased from Beijing Vital River Laboratory Animal Technology Co., Ltd.

2.3 Drug preparation: An appropriate amount of sample was weighed, and an appropriate amount of DMSO and labrasol were added in sequence according to the volume ratio of 10:90, then the mixture was stirred and sonicated to reach a clear state of 15 mg/mL for intragastric administration.

2.4 Administration: 6 male SD rats were divided into 3 groups, after fasting for one night, the intragastric administration group was administered with a volume of 5 mL/kg and a dose of 75 mg/kg.

3. Experimental Operations and Results

Male rats were euthanized at 1, 4 and 8 hours after intragastric administration of compound 1, and eye tissues from 2 eyes of each rat were combined and the concentration of compound in the retina and choroid/sclera was measured.

The LC-MS/MS method was used to determine the content of the test compound in the eye tissues of rats after intragastric administration. The linear range of the method was from 2.00 to 6000 nmol/L; the eye tissue concentration data are presented in Table 3, in which each eye tissue concentration data was obtained from the combined left and right eyes of 2 rats. The eye pharmacokinetic test results of the compounds of the present disclosure are shown in Table 3 below.

TABLE 3

Pharmacokinetic test results of the compounds of the present disclosure in rat eyes

| Number of the compound | Detection time | Concentration of compounds in eye tissue and plasma | | |
|---|---|---|---|---|
| | | Retina (nmol/kg) | Choroid and sclera (nmol/kg) | Plasma (nM) |
| Compound 1 | 1 hour | 90.8 | 640 | 3686 |
| | 4 hours | 147 | 450 | 6442 |
| | 8 hours | ND | 82 | 729 |
| | $AUC_{0-8h}$ (nmol/kg·h or nM·h) | - | 2803 | 22004 |

Note: "-" indicates that the valid values used to calculate this parameter are insufficient and cannot be calculated (the quantifiable values are less than 3).
"ND" means not detected.

Experimental conclusion: The compounds of the present disclosure have a certain amount of drug exposure in both retina and choroid in rat eye fundus.

Experimental Embodiment 4 In Vivo Pharmacodynamic Study of the Compound of the Present Disclosure on Rat DME Model Induced by CA-1 (100 ng)

1. Experimental Design 20 rats were selected from 25 male SD rats and divided into 5 groups according to their body weight, with 4 rats in each group and 1 spare rat in each group, and all the animals were examined by optical coherence tomography before modeling, 48 hours and 72 hours after modeling, respectively. The appropriate scanning position for measurement was selected and the retinal thickness was marked. Through the changes of retinal thickness in each group, the effects of the test compounds on improving retinal edema were compared, and the active compounds were screened. The above experimental operations of modeling and inspection should follow the order of the right eye first and then the left eye.

2. Experimental Materials 2.1. Experimental Animals

Species: Rat
Strain: SD rat, SPF grade
Age and weight: 7-8 weeks old, weighing 250-300 g
Sex: Male
Supplier: Zhejiang Vital River Laboratory Animal Technology Co., Ltd.
Animal certificate number:
2.2 Molding agent
Carbonic anhydrase-1 (CA-1, Sigma)
3. Experimental methods and procedures 3.1 Administration and modeling On the day of modeling, all animals were first administered the vehicle or the test compound orally, and about 4 hours later, the animals were injected with physiological saline (5 µL/eye) or CA-I (100 ng/eye) into the vitreous cavity of both eyes for modeling, and the end time of injection in the second eye was recorded as 0 hour, and the vehicle (10 % DMSO + 90 % labrasol) or the test compound was administered orally to all animals at 4±0.5 hours, 20±0.5 hours, 28±0.5 hours, 44±0.5 hours, 52±0.5 hours and 68±0.5 hours after modeling, respectively.

3.2 Optical Coherence Tomography (OCT) Examination

Before modeling, 48 hours and 72 hours after modeling, animals were first anesthetized, and then examined by optical coherence tomography (OCT), and before anesthesia, appropriate mydriatic agents were used to ensure that the pupils of animals were completely dilated, and the animals were anesthetized by a combination of intramuscular injection of Zoletil (5 mg/kg) and Xylazine solution (3 mg/kg). OCT inspection requirements are as follows:
1) The optic disc should be placed in the center of the infrared fundus image during data collection;
2) the retinal scan was performed in a "pozidriv" type, with the crossover point over the optic disc, and the retina was scanned at the widest length.
3) The software tracking function was used as much as possible for comparison of retinal thickness before and after administration, and if the tracking function was not available, the eye position was adjusted as much as possible to be consistent with that before administration, and the clarity of the tomographic images was ensured as much as possible to facilitate comparison of retinal thickness before and after administration.

4. Experimental Result

The retina of the animals in each group showed normal on

TABLE 4

Experimental protocol of the compound of the present disclosure on rat DME model induced by CA-1

| Group | Administration dose | | | | Molding agent | | | |
|---|---|---|---|---|---|---|---|---|
| | Test compound | dose (mg/kg) | Volume (mL/kg) | Concentration (mg/mL) | Test compound | dose (ng/eye) | Volume (µL/eye) | Concentration (mg/mL) |
| 1 | Vehicle | 0 | 10 | 0 | Physiological saline | 0 | 5 | 0 |
| 2 | Vehicle | 0 | 10 | 0 | CA-I | 100 | 5 | 0.02 |
| 3 | Compound 1 | 75 | 10 | 7.5 | CA-I | 100 | 5 | 0.02 |
| 4 | Compound 1 | 50 | 10 | 5 | CA-I | 100 | 5 | 0.02 |
| 5 | Compound 8 | 75 | 10 | 7.5 | CA-I | 100 | 5 | 0.02 |

OCT examination before modeling, and significant retinal thickening was observed in rats injected with physiological saline only at 48 hours and 72 hours after modeling, and retinal thickening was relieved to different degrees in the orally administered groups, and the low dose group of compound 1 (50 mg/kg) partially relieved the retinal thickening at 48 hours (relief rate was 19 %) and significantly relieved the retinal thickening at 72 hours (relief rate was 79 %), and the high dose group of compound 1 (75 mg/kg) completely relieved the retinal thickening induced by carbonic anhydrase-1 both at 48 hours and 72 hours (relief rate was 100 %). Compound 8 (75 mg/kg) partially relieved retinal thickening at 48 hours (relief rate was 84 %) and completely relieved cretinal thickening induced by carbonic anhydrase-1 at 72 hours (relief rate was 116 %), while the animals exhibited good tolerance to the above test compounds.

What is claimed is:

1. A compound of formula (I) or a pharmaceutically acceptable salt thereof,

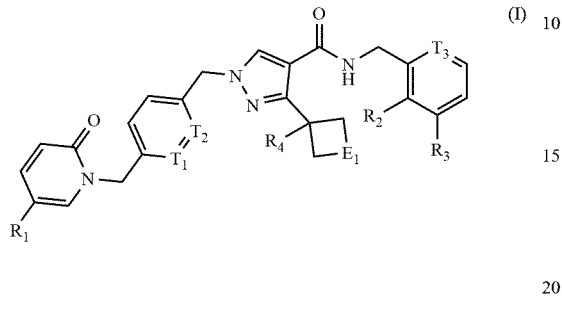
(I)

wherein,
$R_1$ is H, F, Cl, Br, I, OH or $NH_2$;
$R_2$ is H, F, Cl, Br, I, OH or $NH_2$;
$R_3$ is H, F, Cl, Br, I, OH, $C_{1-3}$ alkyl or $C_{1-3}$ alkoxy, wherein the $C_{1-3}$ alkyl and $C_{1-3}$ alkoxy are each independently and optionally substituted by 1, 2 or 3 $R_a$;
$R_4$ is H or $C_{1-3}$ alkyl, wherein the $C_{1-3}$ alkyl is optionally substituted by 1, 2 or 3 $R_b$;
$T_1$ is N or $CR_5$;
$T_2$ is N or $CR_6$;
$T_3$ is N or $CR_7$;
$E_1$ is O or $NR_8$;
$R_5$, $R_6$ and $R_7$ are each independently H, F, Cl, Br, I, OH or $NH_2$;
$R_8$ is H, $C_{1-3}$ alkyl, $C_{1-3}$ alkoxy, —C(=O)$C_{1-3}$ alkyl or —S(=O)$_2$$C_{1-3}$ alkyl, wherein the $C_{1-3}$ alkyl, $C_{1-3}$ alkoxy, —C(=O)$C_{1-3}$ alkyl and —S(=O)$_2$$C_{1-3}$ alkyl are each independently and optionally substituted by 1, 2 or 3 $R_c$;
$R_a$, $R_b$ and $R_c$ are each independently F, Cl, Br, I, OH or $NH_2$.

2. The compound or the pharmaceutically acceptable salt thereof as claimed in claim 1, wherein, $R_3$ is H, F, Cl, Br, I, OH, $CH_3$ or —O—$CH_3$, wherein the $CH_3$ and —O—$CH_3$ are each independently and optionally substituted by 1, 2 or 3 $R_a$.

3. The compound or the pharmaceutically acceptable salt thereof as claimed in claim 2, wherein, $R_3$ is —O—$CH_3$.

4. The compound or the pharmaceutically acceptable salt thereof as claimed in claim 1, wherein, $R_4$ is H or $CH_3$, wherein the $CH_3$ is optionally substituted by 1, 2 or 3 $R_b$.

5. The compound or the pharmaceutically acceptable salt thereof as claimed in claim 4, wherein, $R_4$ is H or $CH_3$.

6. The compound or the pharmaceutically acceptable salt thereof as claimed in claim 1, wherein, $R_8$ is H, $CH_3$, $CH_2$—$CH_3$, —C(=O)—$CH_3$ or —S(=O)$_2$—$CH_3$, wherein the $CH_3$, $CH_2$—$CH_3$, —C(=O)—$CH_3$ or —S(=O)$_2$—$CH_3$ is optionally substituted by 1, 2 or 3 $R_c$.

7. The compound or the pharmaceutically acceptable salt thereof as claimed in claim 6, wherein, $R_8$ is H, $CH_3$, $CH_2$—$CF_3$, —C(=O)—$CH_3$ or —S(=O)$_2$—$CH_3$.

8. The compound or the pharmaceutically acceptable salt thereof as claimed in claim 1, wherein, the compound has the structure of (I-1) or (I-2)

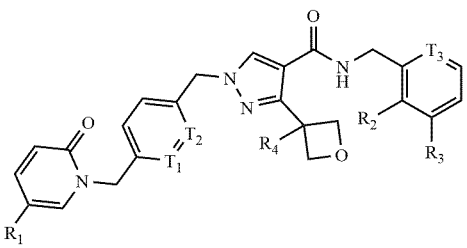
(I-1)

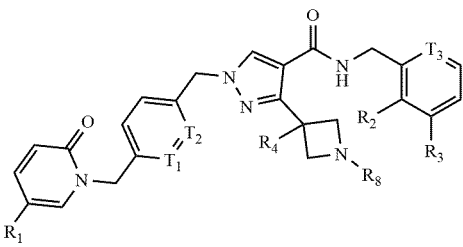
(I-2)

wherein,
$T_1$, $T_2$, $T_3$, $R_1$, $R_2$, $R_3$, $R_4$ and $R_8$ are as defined above.

9. A compound of the following formula or a pharmaceutically acceptable salt thereof, and the compound is:

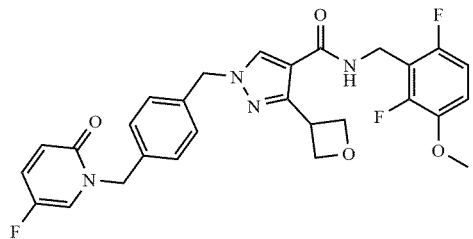 [SMILES: COc1ccc(F)c(CNC(=O)c2cn(Cc3ccc(Cn4cc(F)ccc4=O)cc3)nc2C2COC2)c1F]

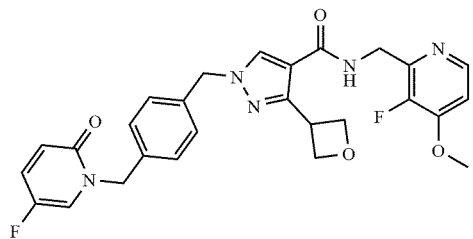 [SMILES: COc1ccnc(CNC(=O)c2cn(Cc3ccc(Cn4cc(F)ccc4=O)cc3)nc2C2COC2)c1F]

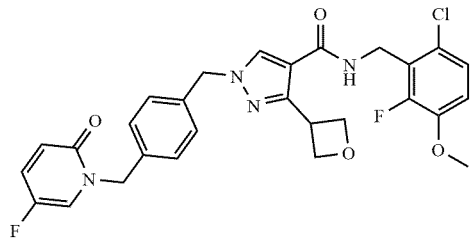 [SMILES: COc1ccc(Cl)c(CNC(=O)c2cn(Cc3ccc(Cn4cc(F)ccc4=O)cc3)nc2C2COC2)c1F]

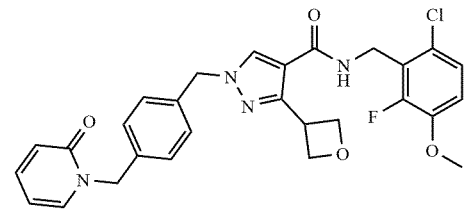 [SMILES: COc1ccc(Cl)c(CNC(=O)c2cn(Cc3ccc(Cn4ccccc4=O)cc3)nc2C2COC2)c1F]

55
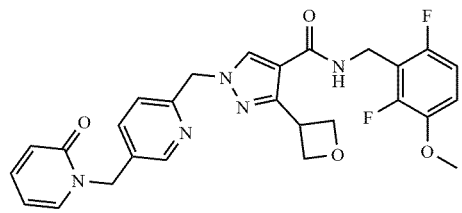 [SMILES: COc1ccc(F)c(CNC(=O)c2cn(Cc3ccc(Cn4ccccc4=O)cn3)nc2C2COC2)c1F]
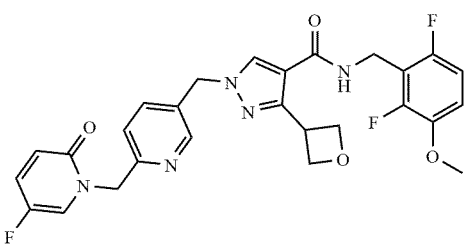 [SMILES: COc1ccc(F)c(CNC(=O)c2cn(Cc3ccc(Cn4cc(F)ccc4=O)nc3)nc2C2COC2)c1F]
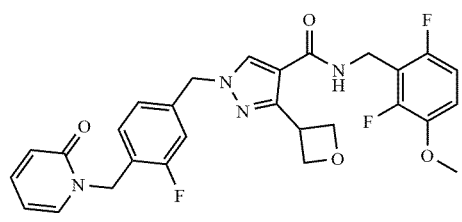 [SMILES: COc1ccc(F)c(CNC(=O)c2cn(Cc3ccc(Cn4ccccc4=O)c(F)c3)nc2C2COC2)c1F]
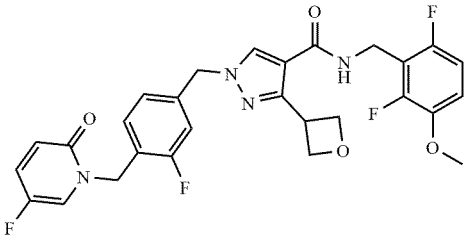 [SMILES: COc1ccc(F)c(CNC(=O)c2cn(Cc3ccc(Cn4cc(F)ccc4=O)c(F)c3)nc2C2COC2)c1F]
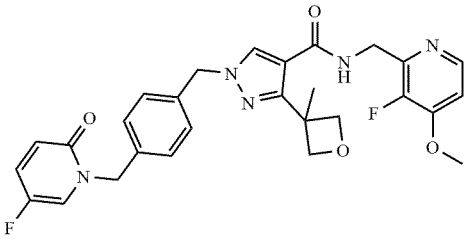 [SMILES: COc1ccnc(CNC(=O)c2cn(Cc3ccc(Cn4cc(F)ccc4=O)cc3)nc2C2(C)COC2)c1F]
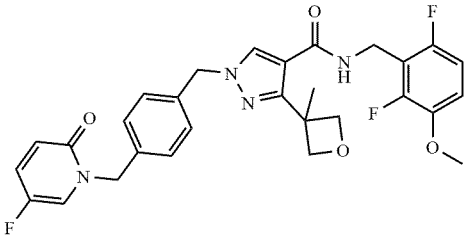 [SMILES: COc1ccc(F)c(CNC(=O)c2cn(Cc3ccc(Cn4cc(F)ccc4=O)cc3)nc2C2(C)COC2)c1F]
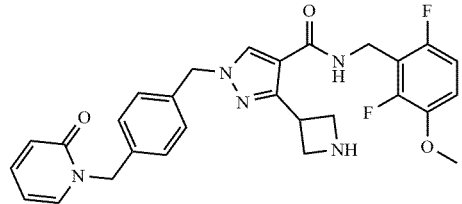 [SMILES: COc1ccc(F)c(CNC(=O)c2cn(Cc3ccc(Cn4ccccc4=O)cc3)nc2C2CNC2)c1F]
56
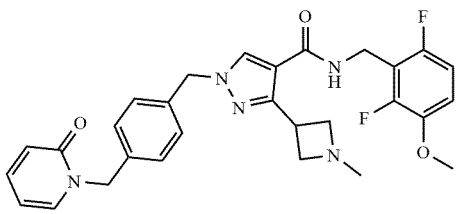 [SMILES: COc1ccc(F)c(CNC(=O)c2cn(Cc3ccc(Cn4ccccc4=O)cc3)nc2C2CN(C)C2)c1F]
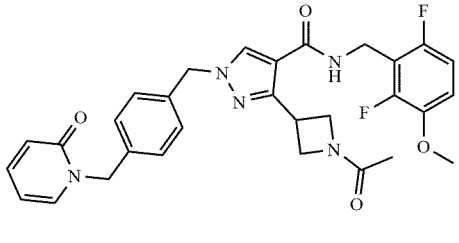 [SMILES: COc1ccc(F)c(CNC(=O)c2cn(Cc3ccc(Cn4ccccc4=O)cc3)nc2C2CN(C(C)=O)C2)c1F]
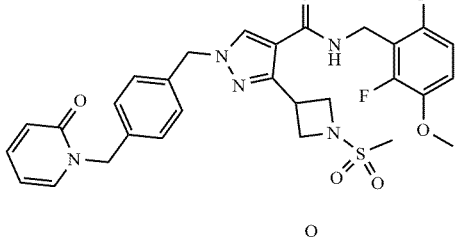
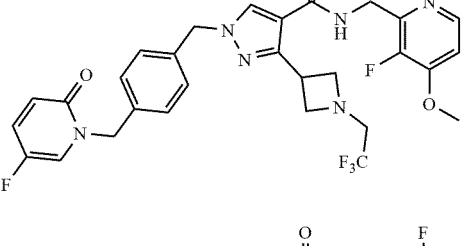
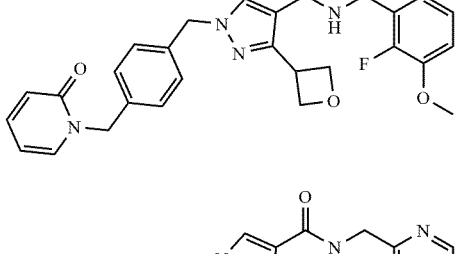
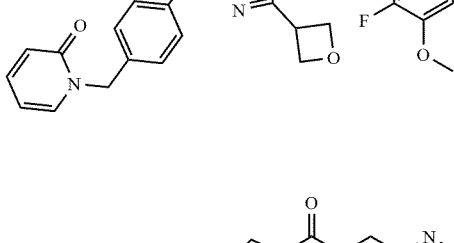
or
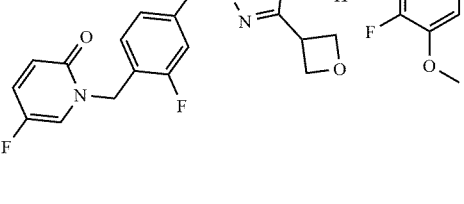

10. The compound or the pharmaceutically acceptable salt thereof as claimed in claim 1, wherein the salt is hydrochloride.

* * * * *